(12) United States Patent
Okumura et al.

(10) Patent No.: US 9,315,856 B2
(45) Date of Patent: Apr. 19, 2016

(54) INSPECTION TOOL FOR NUCLEIC ACID CHROMATOGRAPHY

(71) Applicant: NGK INSULATORS, LTD., Aichi (JP)

(72) Inventors: Hidemasa Okumura, Nagoya (JP); Toshikazu Hirota, Nagoya (JP)

(73) Assignee: NGK INSULATORS, LTD., Aichi-prefecture (JP)

( * ) Notice: Subject to any disclaimer, the term of this patent is extended or adjusted under 35 U.S.C. 154(b) by 0 days.

(21) Appl. No.: 14/580,404

(22) Filed: Dec. 23, 2014

(65) Prior Publication Data

US 2015/0176066 A1 Jun. 25, 2015

Related U.S. Application Data

(63) Continuation of application No. PCT/JP2013/068565, filed on Jul. 5, 2013.

(30) Foreign Application Priority Data

Jul. 6, 2012 (JP) .................. 2012-153114

(51) Int. Cl.
*C12Q 1/68* (2006.01)
*G01N 33/558* (2006.01)

(52) U.S. Cl.
CPC ............ *C12Q 1/6834* (2013.01); *C12Q 1/6813* (2013.01); *G01N 33/558* (2013.01); *C12Q 2565/507* (2013.01)

(58) Field of Classification Search
None
See application file for complete search history.

(56) References Cited

U.S. PATENT DOCUMENTS

| 6,537,828 B1 | 3/2003 | Nakaya et al. |
| 2002/0094585 A1 | 7/2002 | Nakaya et al. |
| 2003/0073121 A1 | 4/2003 | Mendel-Hartvig et al. |

FOREIGN PATENT DOCUMENTS

| JP | 11-44689 A | 2/1999 |
| JP | 2001-157598 A | 6/2001 |
| JP | 2005-503556 A | 2/2005 |
| JP | 2006-201062 A | 8/2006 |
| JP | 2010-014507 A | 1/2010 |
| WO | WO03/025573 A1 | 3/2003 |

OTHER PUBLICATIONS

English language translation of Written Opinion for PCT Patent App. No. PCT/JP2013/068565 (Jul. 30, 2013).
International Search Report for PCT Patent App. No. PCT/JP2013/068565 (Jul. 30, 2013) with English translation.
Written Opinion for PCT Patent App. No. PCT/JP2013/068565 (Jul. 30, 2013).

*Primary Examiner* — Jill Warden
*Assistant Examiner* — Timothy G Kingan
(74) *Attorney, Agent, or Firm* — Cermak Nakajima & McGowan LLP; Tomoko Najajima

(57) ABSTRACT

An inspection tool for nucleic acid chromatography includes an elongated porous sheet and a backing member. The porous sheet has a surface including a detection surface that has a strip-shaped indication portion where a nucleic acid probe for capturing the target nucleic acid is fixed. The backing member has an attached surface in a concave shape. The porous sheet has a warped shape following the concave shape of the attached surface.

9 Claims, 14 Drawing Sheets

INSPECTION TOOL FOR NUCLEIC ACID CHROMATOGRAPHY

TECHNICAL FIELD

The present invention relates to an inspection tool for nucleic acid chromatography usable for a diagnosis related to an infection, an allergy, and the like and for detecting a bacteria, a virus, and the like.

BACKGROUND ART

It is possible to examine the presence or absence of a nucleic acid (DNA or RNA) originating in a virus or a bacteria and the presence or absence of a nucleic acid originating in the mutant gene related to a specific disease or diathesis so as to accurately diagnose an infection, a genetic disorder such as a tumor, a diathesis, and the like. For example, for diagnosing the presence or absence of a viral infection, a specimen is obtained from the mucous membrane of the patient and the like to perform a process for amplifying only the nucleic acid originating in the virus using a PCR method. When the nucleic acid originating in the virus is detected in the specimen obtained in this process, the patient can be determined to be infected by the virus. Nowadays, the development of genome analysis causes accumulation of information related to the base sequence of the nucleic acid such as a gene. Additionally, the improvement of the PCR method facilitates selectively amplifying the nucleic acid originating in the virus or in the bacteria or the nucleic acid originating in the specific mutant gene. Therefore, for further popularization of the application of the above-described diagnosis method for the nucleic acid, there is the need for a technique for simply determining presence or absence of a specific nucleic acid.

As a technique for simply determining the presence or absence of the specific nucleic acid (hereinafter referred to as "the target nucleic acid"), there is proposed an inspection tool for nucleic acid chromatography (in Patent Documents 1 and 2). This inspection tool for nucleic acid chromatography expands a liquid specimen in a porous sheet using a system similar to that of paper chromatography, and captures the target nucleic acid contained in the specimen using a nucleic acid probe fixed to the surface of the porous sheet. Furthermore, the captured target nucleic acid is colored to indicate the detection of the target nucleic acid on the surface of the porous sheet. Thus, in the inspection tool for nucleic acid chromatography, in the case where the target nucleic acid is contained in the specimen, the indication appears on the surface of the porous sheet. On the other hand, in the case where the target nucleic acid is not contained in the specimen, the indication does not appear on the surface of the porous sheet. with this extremely simple system, it is possible to determine the presence or absence of the target nucleic acid.

Typically, the inspection tool for nucleic acid chromatography is widely used as a test piece (this is ordinarily referred to as "the strip") made by attaching the porous sheet in an elongated rectangular shape to a board (backing sheet) in an elongated rectangular shape (in Patent Documents 3 and 4). For example, in the case where the target nucleic acid is labeled with dye in advance when the specimen is prepared, insertion of the distal end portion of the above-described strip into a test tube containing the specimen causes capillary action to expand the specimen in the porous sheet without any subsequent operation. Then, the target nucleic acid is captured and accumulated in the position where the nucleic acid probe is fixed in the porous sheet. This allows coloring the porous sheet surface (in the portion where the nucleic acid probe is fixed). Accordingly, multiple specimens can be simultaneously inspected even with a very simple work of only inserting the strips of the inspection tool for nucleic acid chromatography in respective multiple test tubes, as an advantage.

CITATION LIST

Patent Documents

Patent Document 1: JP-A-2001-157598
Patent Document 2: JP-A-2005-503556
Patent Document 3: JP-A-2006-201062
Patent Document 4: JP-A-2010-14507

SUMMARY OF THE INVENTION

Problem to be Solved by the Invention

However, in the strip of the above-described inspection tool for nucleic acid chromatography, in the case where the concentration of the target nucleic acid in the specimen is low, the color of indication, which indicates the detection of the target nucleic acid, becomes faint and blurry and it is difficult to determine the presence of the target nucleic acid in some cases (as a first problem of the conventional technique)

The strip of the above-described inspection tool for nucleic acid chromatography is the elongated and thin test piece. Accordingly, in the case where the strip is observed from the direction other than the front view, in particular, in the case where the strip is observed from the side view, the surface of the porous sheet becomes difficult to be confirmed visually. As a result, it becomes difficult to determine the presence or absence of the indication indicative of the detection of the target nucleic acid (a second problem of the conventional technique). There seems to be no problem as long as the strip is turned toward the front by handling the strip during observation. However, when the porous sheet is touched during the handling, the porous sheet is contaminated and the color might not appear although the target nucleic acid is captured. As a result, the specimen where the target nucleic acid is present might be incorrectly determined that the target nucleic acid is not present. Additionally, the strip of the inspection tool for nucleic acid chromatography has the important advantage that allows simultaneously and simply inspecting multiple specimens as described above. Therefore, adjusting the directions of the strips one by one by handling significantly ruins this important advantage.

In view of the first problem of the above-mentioned conventional techniques, and an object of a first invention of this application is to provide a technique that allows simply determining the presence or absence of the target nucleic acid also in the case where the concentration of the target nucleic acid in the specimen is low.

In view of the second problem of the above-mentioned conventional techniques, and an object of a second invention of this application is to provide a technique that allows simply determining the presence or absence of the indication indicative of detection of a target nucleic acid also in the case where the inspection tool for nucleic acid chromatography is observed from the direction other than the front view.

Means for Solving the Problem

The present invention is the inspection tool for nucleic acid chromatography as follows.

[1] An inspection tool for nucleic acid chromatography includes: an elongated porous sheet that expands a sample liquid containing a target nucleic acid and detects the target nucleic acid so as to indicate the detection; and a backing member having an attached surface where the porous sheet is attached. The porous sheet has a surface including a detection surface. The detection surface includes a strip-shaped indication portion where a nucleic acid probe for capturing the target nucleic acid is fixed. The indication portion extends at an angle to intersect with a longitudinal direction of the porous sheet. The attached surface has a concave shape. The porous sheet has a warped shape following the concave shape of the attached surface.

[2] In the inspection tool for nucleic acid chromatography according to [1] described above, the attached surface has a concave shape in a cross section that is parallel to the longitudinal direction of the porous sheet and parallel to a thickness direction of the porous sheet.

[3] In the inspection tool for nucleic acid chromatography according to [1] or [2] described above, the detection surface has a smaller average opening diameter than an average opening diameter on a surface on the attached surface side of the porous sheet in association with warping of the porous sheet.

[4] In the inspection tool for nucleic acid chromatography according to any of [1] to [3] described above, the backing member is an elongated plate, and a longitudinal direction of the backing member is parallel to the longitudinal direction of the porous sheet.

[5] In the inspection tool for nucleic acid chromatography according to any of [1] to [4] described above, the porous sheet is warped with a curvature.

[6] In the inspection tool for nucleic acid chromatography according to [5] described above, the porous sheet has a depression value of 1.0 to 5.0 mm.

[7] In the inspection tool for nucleic acid chromatography according to any of [1] to [6] described above, the backing member has a surface on an opposite side of the attached surface in a protruding shape complementary to the concave shape of the attached surface so as to be arched.

[8] An inspection tool set for nucleic acid chromatography includes: a plurality of the inspection tools for nucleic acid chromatography according to any of [1] to [7] described above; and a packing case that houses the inspection tool for nucleic acid chromatography.

[9] An inspection tool set for nucleic acid chromatography includes: a plurality of the inspection tools for nucleic acid chromatography according to [7] described above; and a packing case that houses the inspection tool for nucleic acid chromatography. The respective backing members of the plurality of the inspection tools for nucleic acid chromatography are arched with different curvatures.

[10] An inspection tool for nucleic acid chromatography includes: an elongated porous sheet that expands a sample liquid containing a target nucleic acid and detects the target nucleic acid so as to indicate the detection; and a backing member where the porous sheet is attached. The porous sheet has a surface including a detection surface. The detection surface includes a strip-shaped indication portion where a nucleic acid probe for capturing the target nucleic acid is fixed. The indication portion extends at an angle to intersect with a longitudinal direction of the porous sheet. In a cross section of the indication portion taken perpendicularly to the detection surface and along an extending direction of the indication portion, a portion other than both end portions of the indication portion projects out with respect to a reference line coupling both the end portions of the indication portion.

[11] In the inspection tool for nucleic acid chromatography according to [10] described above, in the cross section perpendicular to the longitudinal direction of the porous sheet, the detection surface project out while having a curvature.

[12] In the inspection tool for nucleic acid chromatography according to [10] or [11] described above, in the indication portion, the nucleic acid probe is fixed at a higher density in a region having a predetermined width from each of both the end portions of the indication portion toward a center compared with in a residual region in the same indication portion.

[13] In the inspection tool for nucleic acid chromatography according to any of [10] to [12] described above, in the indication portion, the porous sheet has a smaller average aperture diameter in a region having a predetermined width from each of both the end portions of the indication portion toward a center compared with in a residual region in the same indication portion.

Effect of the Invention

According to the first invention (the inventions described in [1] to [9] above) of this application, the backing member of the inspection tool for nucleic acid chromatography has the attached surface in the concave shape. The porous sheet has the warped shape following the concave shape of this attached surface, and consequently that in the indication portion, the target nucleic acids are captured while being densely gathered more. As a result, a thick color of indication indicative of the detection of the target nucleic acid is likely to appear. That is, according to the first invention (the inventions described in [1] to [9] above) of this application, since a thick color of indication indicative of the detection of the target nucleic acid is likely to appear, it is possible to simply determine the presence or absence of the target nucleic acid also in the case where the concentration of the target nucleic acid in the specimen is low.

According to the second invention (the inventions described in [10] to [13] above) of this application, in the indication portion indicating the detection of the target nucleic acid, the portion other than both the end portions projects out compared with both the end portions of the indication portion. Accordingly, a part of the indication portion is viewable as a. surface also in the case where the inspection tool for nucleic acid chromatography is observed from the direction other than the front view. As a result, it is possible to simply determine the presence or absence of indication indicative of the detection of the target nucleic acid.

MODE FOR CARRYING OUT THE INVENTION

Hereinafter, embodiments of the present invention will be described with reference to the drawings. The present invention is not limited to the following embodiments, and changes, modifications and improvements can be added to the embodiments without departing from the gist of the present invention.

Figure 1A:
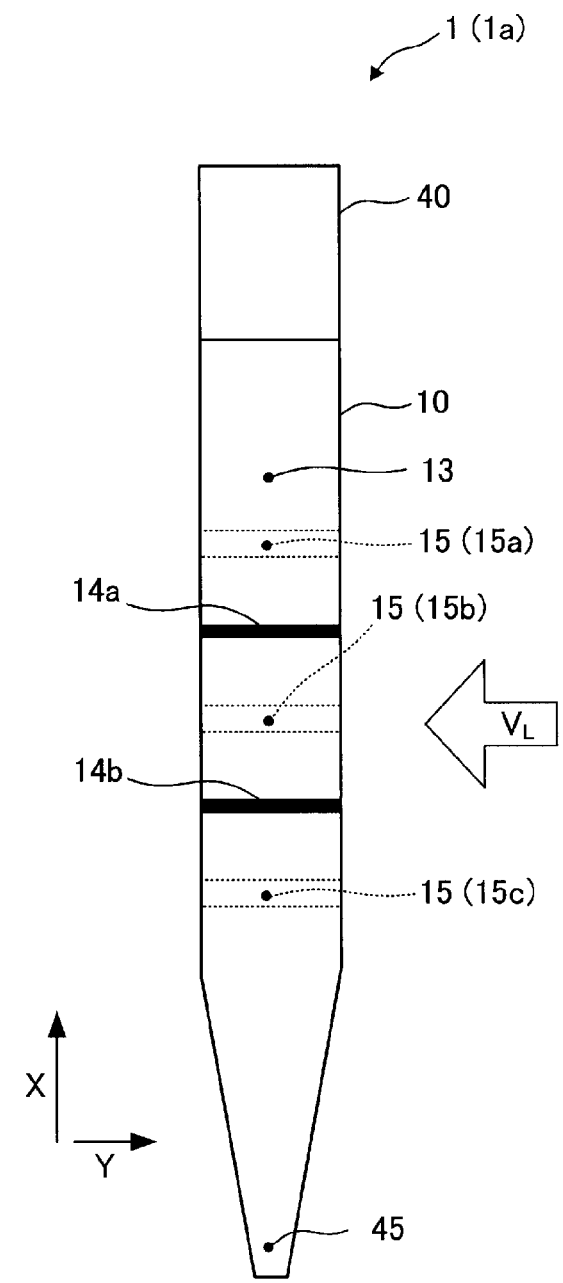
FIG. 1A is a front view schematically showing an embodiment of an inspection tool for nucleic acid chromatography according to a first invention.
Figure 1B:
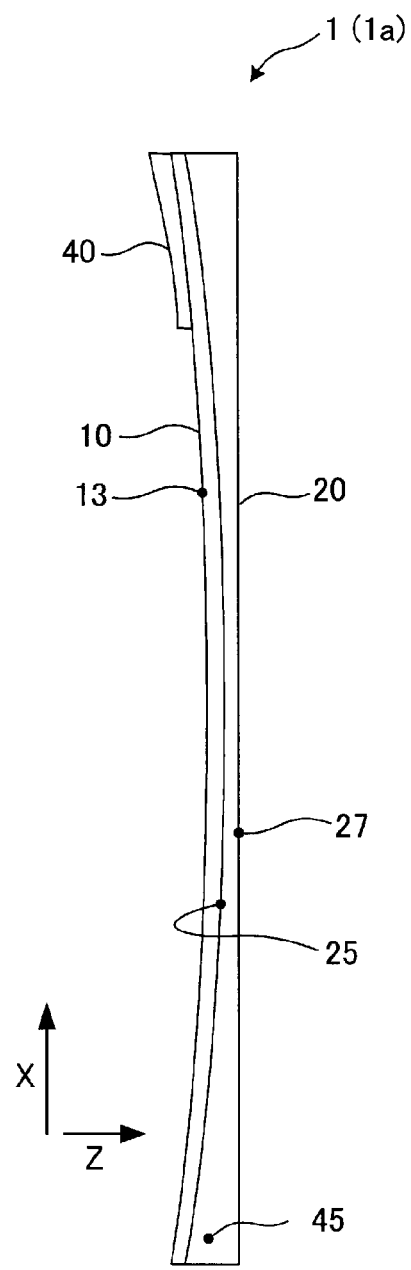
FIG. 1B is a schematic side view of an inspection tool for nucleic acid chromatography viewed from the direction of an outlined arrow $V_L$ shown in FIG. 1A.

1. First Invention:

FIG. 1A is a front view schematically showing an embodiment of an inspection tool for nucleic acid chromatography according to the first invention of this application. FIG. 1B is a schematic side view of an inspection tool 1a for nucleic acid chromatography viewed from the direction of an outlined arrow $V_L$ shown in FIG. 1A. The inspection tool 1a for nucleic acid chromatography according to this embodiment includes a porous sheet 10 in an elongated shape and a backing member 20. Furthermore, the inspection tool 1a for nucleic acid chromatography according to this embodiment includes an absorbent pad 40.

Firstly, the inspection tool 1a for nucleic acid chromatography according to this embodiment includes a detection surface 13 on the surface of the porous sheet 10. On the detection surface 13, an indication appears when a target nucleic acid is detected. In this detection surface 13, an indication portion 15 is disposed. The indication portion 15 is a strip-shaped region that extends at an angle to intersect with the longitudinal direction X of the porous sheet 10. Within this strip-shaped region, a nucleic acid probe for capturing the target nucleic acid is fixed.

Additionally, as shown in FIG. 1B, the inspection tool 1a for nucleic acid chromatography according to this embodiment includes a concave-shaped attached surface 25 on the backing member 20. The porous sheet 10 is attached to the attached surface 25 in a warped shape while following the concave shape of this attached surface 25. Accordingly, in the porous sheet 10, the detection surface 13 and the indication portion 15, which is a part of the region of the detection surface 13, also have arched shapes.

Figure 2:
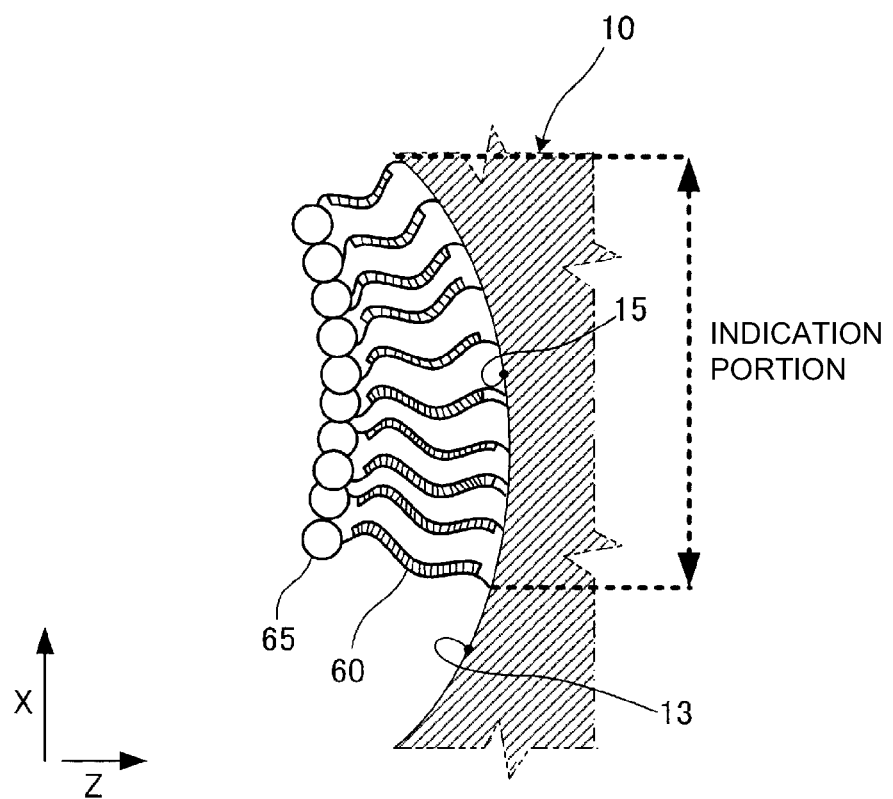
FIG. 2 is an explanatory diagram schematically showing the state where target nucleic acids are captured in an indication portion when the inspection tool for nucleic acid chromatography shown in FIG. 1A is used.

FIG. 2 is an explanatory diagram schematically showing the state where target nucleic acids 60 are captured in the indication portion 15 when the inspection tool 1a for nucleic acid chromatography shown in FIG. 1A is used. As shown in the drawing, in the inspection tool 1a for nucleic acid chromatography according to this embodiment, the indication portion 15 has the arched shape. Accordingly, the target nucleic acids 60 captured in the indication portion 15, in particular, the portions distant from the indication portion 15 in the target nucleic acid 60 gather together. As a result, respective dyes 65 that label the target nucleic acids 60 are densely gathered. This dense gathering of the dyes 65 is likely to cause a thick and clear signal (color) indicative of the detection of the target nucleic acid 60 to appear in indication portion 15 in the inspection tool 1a for nucleic acid chromatography according to this embodiment.

In the inspection tool 1a for nucleic acid chromatography according to this embodiment, the attached surface 25 is preferred to have a concave shape in the cross section that is parallel to the longitudinal direction X of the porous sheet 10 and parallel to the thickness direction Z of the porous sheet 10. In the case where the attached surface 25 has the depressed shape as an arch shape along the longitudinal direction X as described above, the target nucleic acids 60 gather together from the side toward the center of the strip-shaped indication portion 15. Accordingly, the signal (color) indicative of the detection of the target nucleic acid 60 is likely to appear as a sharp band.

In the inspection tool 1a for nucleic acid chromatography of this embodiment, the respective target nucleic acids 60 captured in the indication portion 15 further gather together. As a result, the respective dyes 65 labeling the target nucleic acids 60 are further densely gathered. Accordingly, the average opening diameter in the detection surface 13 is preferred to be smaller than the average opening diameter in the surface on the attached surface 25 side of the porous sheet 10 in association with the warping of the porous sheet 10.

Figure 3:
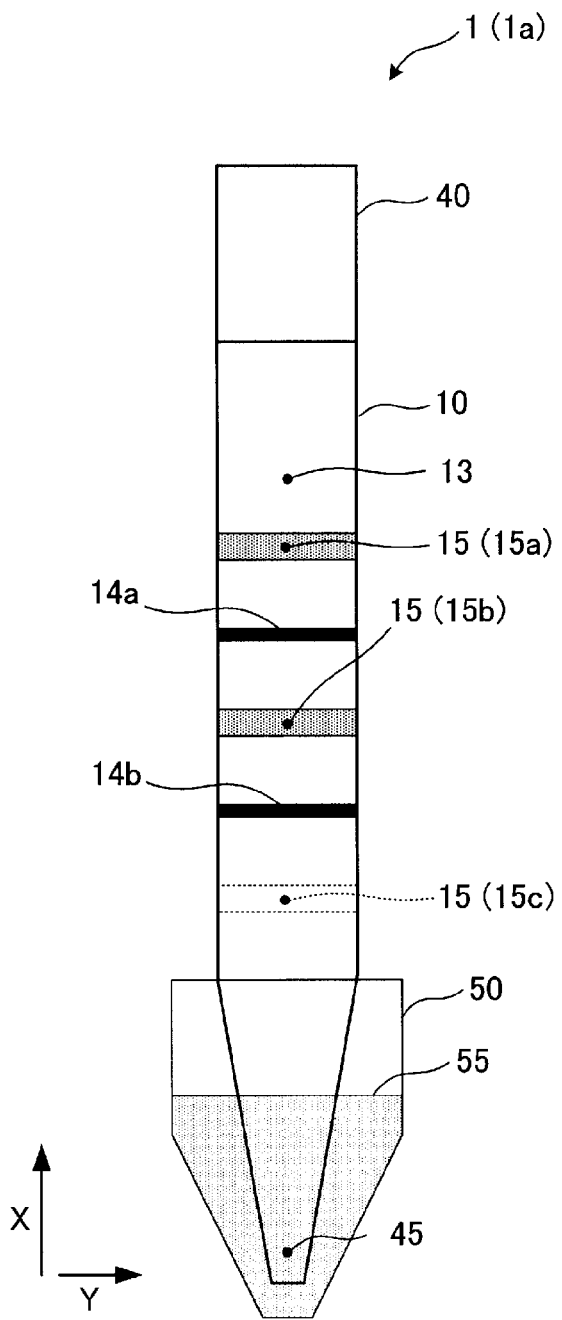
FIG. 3 is a schematic diagram showing one mode of use of the inspection tool for nucleic acid chromatography shown in FIG. 1A.

FIG. 3 is a schematic diagram showing one mode of use of the inspection tool 1a for nucleic acid chromatography shown in FIG. 1A. As shown in the drawing, the inspection tool 1a for nucleic acid chromatography according to this embodiment can be used such that, for example, a distal end portion 45 of the inspection tool 1a for nucleic acid chromatography is dipped in a liquid specimen 55 contained in a test tube 50. Thus, when the distal end portion 45 is dipped in the specimen 55, the specimen 55 expands within the porous sheet 10 due to a capillary action and is transported to another distal end portion (the distal end portion where the absorbent pad 40 is disposed). At this time, when the target nucleic acid is contained in the specimen 55, this target nucleic acid is captured by the nucleic acid probe fixed to the indication portion 15. As a result, the indication portion 15 is colored by the dye for labeling the target nucleic acid (see indication portions 15a and 15b in FIG. 3).

As shown in FIG. 3, in the inspection tool 1a for nucleic acid chromatography according to this embodiment, the detection surface 13 is partitioned into three areas along the longitudinal direction X by two position markers 14a and 14b. In these three areas, respective indication portions 15a to 15c are disposed one by one. To the indication portions 15a to 15c, respective nucleic acid probes are fixed to capture different types of target nucleic acid (target nucleic acids with different base sequences). For example, a nucleic acid probe for a target nucleic acid as a marker of an allergic disease is fixed to the indication portion 15a, a nucleic acid probe for a target nucleic acid as a tumor marker is fixed to the indication portion 15b, and a nucleic acid probe for a target nucleic acid as a marker of a viral infection is fixed to the indication portion 15c. This allows determining whether or not the person suffers from the above-described three types of diseases by one inspection. Assuming that this configuration is applied to the example shown in FIG. 3, regarding the patient from which the specimen 55 is obtained in FIG. 3, the colors are observed in the indication portions 15a and 15b while no color is observed in the indication portion 15c. The patient is determined to suffer from an allergic disease and a tumor but not to suffer from a viral infection.

In the inspection tool 1a for nucleic acid chromatography according to this embodiment, the indication portions 15a to 15c each extend in a straight line along the width direction Y perpendicular to the longitudinal direction X. In this embodiment, the indication portion 15 need not extend in a straight line along the width direction Y of the porous sheet 10. It is only necessary to dispose the indication portion so that the specimen 55 crosses the indication portion 15 in the course of expansion of the specimen 55 in the porous sheet 10. Although the illustration is omitted here, for example, the indication portion 15 can employ any shape such as a strip shape extending at an angle to intersect with the longitudinal direction X at 45 degrees and a meandering strip shape (for example, see FIG. 9).

The inspection tool 1a for nucleic acid chromatography according to this embodiment includes the absorbent pad 40, which is in contact with a part of the porous sheet 10 and absorbs the specimen 55 having expanded in the porous sheet 10. In the case where the absorbent pad 40 is disposed like the inspection tool 1a for nucleic acid chromatography according to this embodiment, the absorbent pad 40 can absorb and hold the specimen 55 having expanded in the porous sheet 10. This allows increasing the liquid amount of the specimen 55 to expand in the porous sheet 10. Thus, this also allows increasing the amount of the target nucleic acid applied to the inspection tool 1a for nucleic acid chromatography. As a result, the amount of the target nucleic acid to be captured in the indication portion 15 is increased and the signal (color) indicative of the detection of the target nucleic acid appears to be thick. Thus, this configuration is preferred.

In the inspection tool 1a for nucleic acid chromatography according to this embodiment, all or a part of the target nucleic acid is prepared to have a single-stranded polynucleotide structure when the specimen 55 expands in the porous sheet 10. Additionally, the nucleic acid probe to be used at least partially has a single-stranded polynucleotide structure (a single-stranded polynucleotide with the base sequence complementary to the base sequence of the single-stranded polynucleotide of the target nucleic acid) that can be specifically hybridized with the single-stranded polynucleotide structure of the target nucleic acid. With use of these target nucleic acid and nucleic acid probe, when the target nucleic acid reaches the indication portion 15, the single-stranded polynucleotide structure of the target nucleic acid and the single-stranded polynucleotide structure of the nucleic acid probe are hybridized with each other (form a double strand). Then, the target nucleic acid is fixed to the indication portion 15 via the nucleic acid probe. Here, in the inspection tool 1a for nucleic acid chromatography according to this embodiment, the nucleic acid probe is not specifically limited and may be, for example, a DNA probe, an RNA probe, or Morpholino Antisense Oligo insofar as the nucleic acid probe has the single-stranded polynucleotide structure that can be specifically hybridized with the single-stranded polynucleotide structure of the target nucleic acid.

Additionally, the target nucleic acid can also employ a single-stranded DNA, a double-stranded DNA or RNA having an end portion in a single-stranded structure, and the like. A generally available method only needs to be applied to the labeling of the target nucleic acid. In the case where the target nucleic acid is prepared using the PCR method, it is possible to use a method for directly labeling a PCR product using at least one of dNTPs (dATP, dCTP, dGTP, and dTTP) labeled in advance as substrates for the polymerase reaction. Alternatively, it is possible to use a method for adding a label to a PCR product (double-stranded DNA) with no label afterward. The method for adding a label to a PCR product (double-stranded DNA) with no label afterward can employ, for example, a PCR primer that is modified such that both ends of the PCR product have single-stranded polynucleotide structures of specific base sequences. This modified PCR primer is used to obtain a PCR product, and the single-stranded polynucleotide structure of the obtained PCR product is hybridized with a labeled single-stranded polynucleotide having the base sequence complementary to this structure. As a result of this hybridization, the target nucleic acid (PCR product) can be labeled.

In the inspection tool 1a for nucleic acid chromatography according to this embodiment, the porous sheet 10 can employ a sheet with countless pores made of nitrocellulose, cellulose, polyethersulfone, nylon, PVDF, and the like.

Like the inspection tool 1a for nucleic acid chromatography according to this embodiment, the shape of the backing member 20 is preferred to be an elongated plate shape and the longitudinal direction X of the backing member 20 is preferred to be parallel to the longitudinal direction X of the porous sheet 10. Thus, the inspection tool 1a for nucleic acid chromatography is formed as a compact strip, thus being excellent in handling ability.

In the inspection tool 1a for nucleic acid chromatography according to this embodiment, the porous sheet 10 is preferred to be warped with a curvature because the specimen 55 becomes likely to uniformly expand in the porous sheet 10 and as a result the signal (color) appearing in the indication portion 15 becomes less likely to have unevenness. Here, "warped with a curvature" means the state where the porous sheet has an arc shape in the cross-sectional view.

In the inspection tool 1a for nucleic acid chromatography according to this embodiment, in the case where the porous sheet 10 is warped with a curvature, the depression value of the porous sheet 10 is preferred to be 1.0 to 5.0 mm because the signal (color) appearing in the indication portion 15 more reliably becomes less likely to have unevenness. Furthermore, the depression value is more preferred to be 2.0 to 5.0 mm because the handling ability becomes enhanced. Further, in particular, the depression value is further preferred to be 2.0 to 4.0 mm because the signal (color) appearing in the indication portion 15 becomes thick. In the description with reference to FIG. 4, "the depression value of the porous sheet" in this description means the value of a depth D of the depression in the porous sheet to be measured along the direction perpendicular to the longitudinal direction [the direction along which the maximum length of the backing member 20 is measured in the case where the length is measured with a vernier scale (the longitudinal direction X in the example of FIG. 4)] of the above-described backing member 20.

Furthermore, in the inspection tool 1a for nucleic acid chromatography according to this embodiment, it is preferred that the length of the porous sheet 10 be 15 to 100 mm and the depression value be 1.0 to 5.0 mm because the signal (color)

appearing in the indication portion 15 becomes thick. Additionally, it is more preferred that the length of the porous sheet 10 be 30 to 60 mm and the depression value be 1.0 to 4.0 mm. In particular, it is further preferred that the length of the porous sheet 10 be 40 to 50 mm and the depression value be 1.0 to 3.0 mm. The length of the porous sheet in this description means the length of the center line drawn on the porous sheet along the longitudinal direction on the surface (the detection surface) of the porous sheet.

Figure 4:
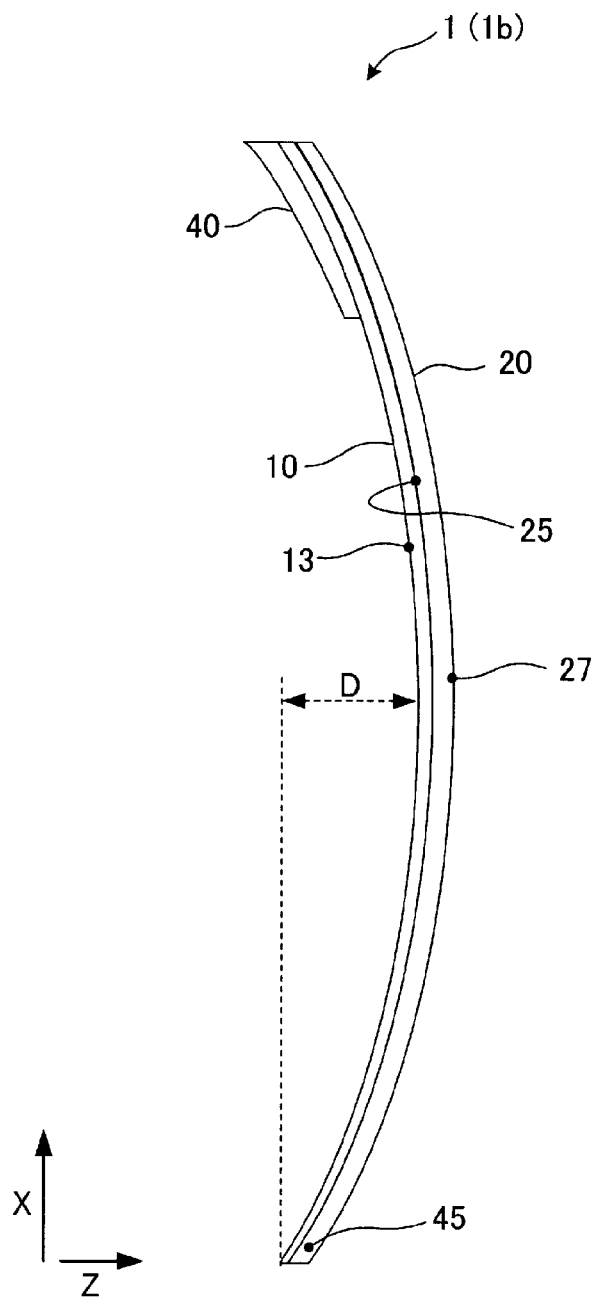
FIG. 4 is schematic side view showing another embodiment of the inspection tool for nucleic acid chromatography according to the first invention.

FIG. 4 is schematic side view showing another embodiment of the inspection tool for nucleic acid chromatography according to the first invention. In an inspection tool 1b for nucleic acid chromatography according to this embodiment, the backing member 20 is arched since a back surface 27 (the surface of the backing member 20 on the opposite side of the attached surface 25) has a protruding shape complementary to the concave shape of the attached surface 25. In the inspection tool 1b for nucleic acid chromatography according to this embodiment, when the back surface 27 of the backing member 20 is placed on a flat lab bench, a clearance occurs between: both ends of the inspection tool 1b for nucleic acid chromatography, and the lab bench since the backing member 20 is arched. This clearance facilitates holding the inspection tool 1b for nucleic acid chromatography. This ease of holding allows preventing the detection surface 13 of the inspection tool 1b for nucleic acid chromatography from being erroneously touched and contaminated, thus preventing erroneous determination due to contamination of the detection surface 13.

Figure 5:
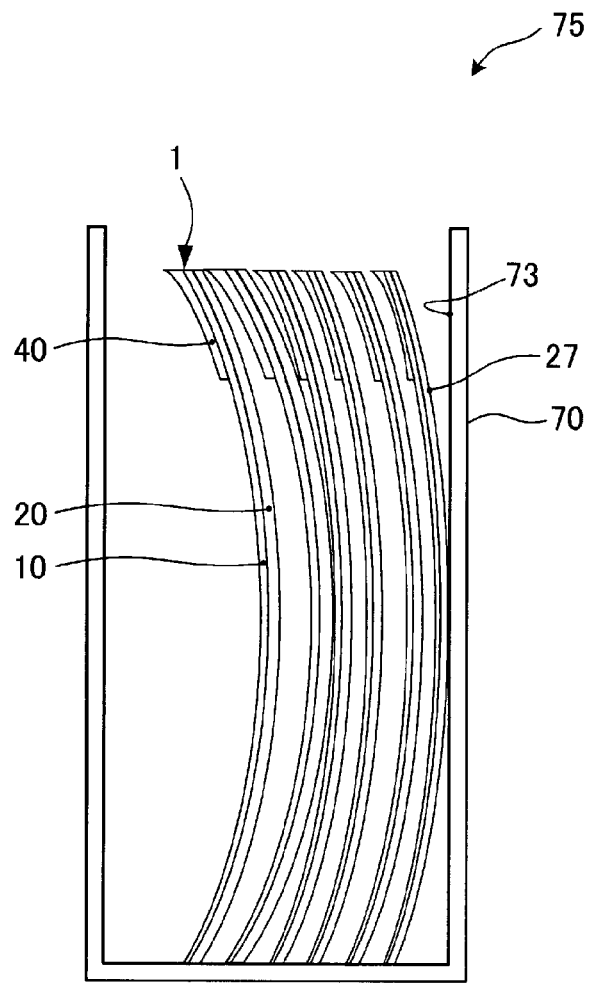
FIG. 5 is a schematic diagram showing an embodiment of an inspection tool set for nucleic acid chromatography according to the first invention.

FIG. 5 is a schematic diagram showing one embodiment of an inspection tool set for nucleic acid chromatography according to the first invention. As shown in the drawing, an inspection tool set 75 for nucleic acid chromatography according to this embodiment includes the above-described inspection tool 1 for nucleic acid chromatography and a packing case 70, which houses the inspection tool 1 for nucleic acid chromatography.

In particular, the inspection tool set 75 for nucleic acid chromatography according to this embodiment includes a plurality of the inspection tools 1 for nucleic acid chromatography whose backing members 20 are arched. Furthermore, the respective backing members 20 of these plurality of inspection tools 1 for nucleic acid chromatography are preferred to be arched with different curvatures. As just described, in the case where the respective backing members 20 of the inspection tools 1 for nucleic acid chromatography are arched with the different curvatures, clearances occur between the respective adjacent inspection tools 1 for nucleic acid chromatography in the packing case 70. As a result, this facilitates picking out the inspection tools 1 for nucleic acid chromatography one by one from the packing case 70. In the case where the backing members 20 of the inspection tools 1 for nucleic acid chromatography are arched with the different curvatures, a clearance occurs between the back surface 27 of the backing member 20 and an inner wall 73 of the packing case 70. This facilitates picking out the inspection tool 1 for nucleic acid chromatography from the packing case 70.

Figure 6A:
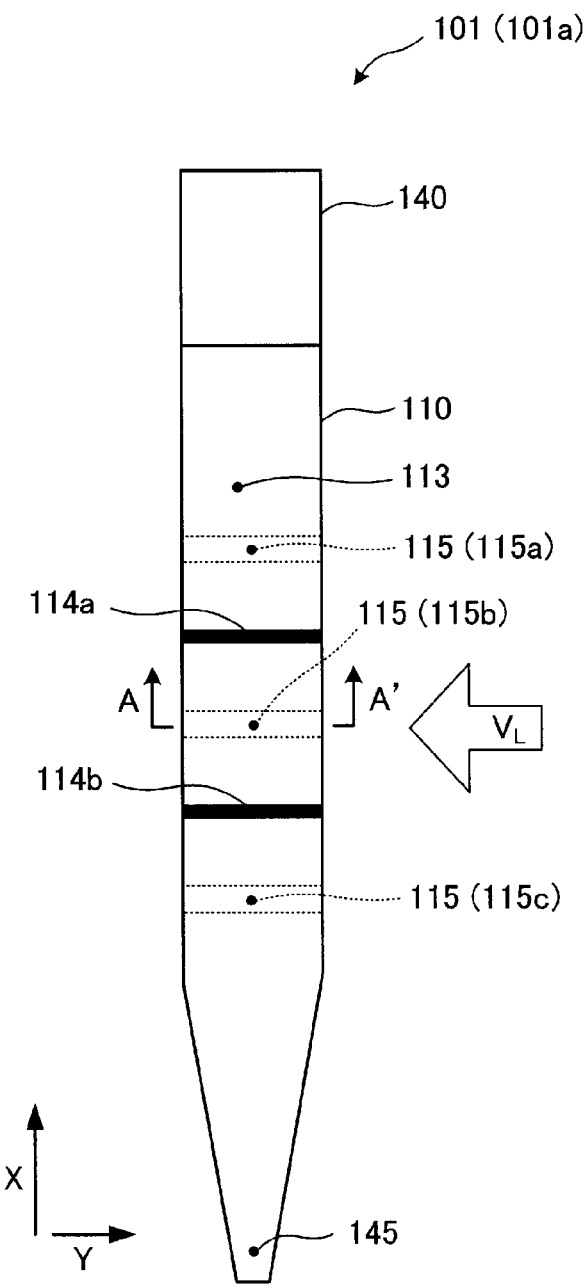
FIG. 6A is a front view schematically showing an embodiment of an inspection tool for nucleic acid chromatography according to a second invention.
Figure 6B:
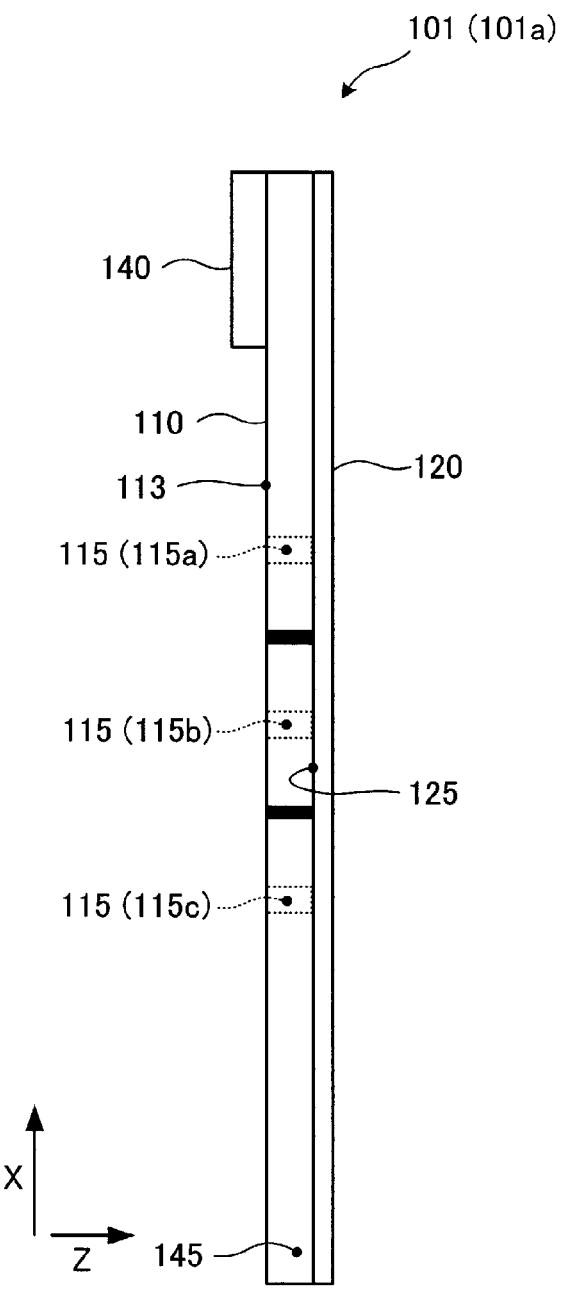
FIG. 6B is a schematic side view of an inspection tool for nucleic acid chromatography viewed from the direction of an outlined arrow $V_L$ shown in FIG. 6A.

2. Second Invention:

FIG. 6A is a schematic front view showing one embodiment of an inspection tool for nucleic acid chromatography according to the second invention of this application. FIG. 6B is a schematic side view of an inspection tool 101a for nucleic acid chromatography observed from the direction (the side) of an outlined arrow $V_L$ shown in FIG. 6A. The inspection tool 101a for nucleic acid chromatography according to this embodiment includes a porous sheet 110 in an elongated shape and a backing member 120. Furthermore, the inspection tool 101a for nucleic acid chromatography according to this embodiment includes an absorbent pad 140.

Firstly, the inspection tool 101a for nucleic acid chromatography according to this embodiment includes a detection surface 113 on the surface of the porous sheet 110. On the detection surface 113, an indication appears when a target nucleic acid is detected. In this detection surface 113, an indication portion 115 is disposed. The indication portion 115 is a strip-shaped region that extends at an angle to intersect with the longitudinal direction X of the porous sheet 110. Within this strip-shaped region, a nucleic acid probe for capturing the target nucleic acid is fixed. Furthermore, in the inspection tool 101a for nucleic acid chromatography according to this embodiment, the porous sheet 110 is attached to an attached surface 125 of the backing member 120.

Figure 7:
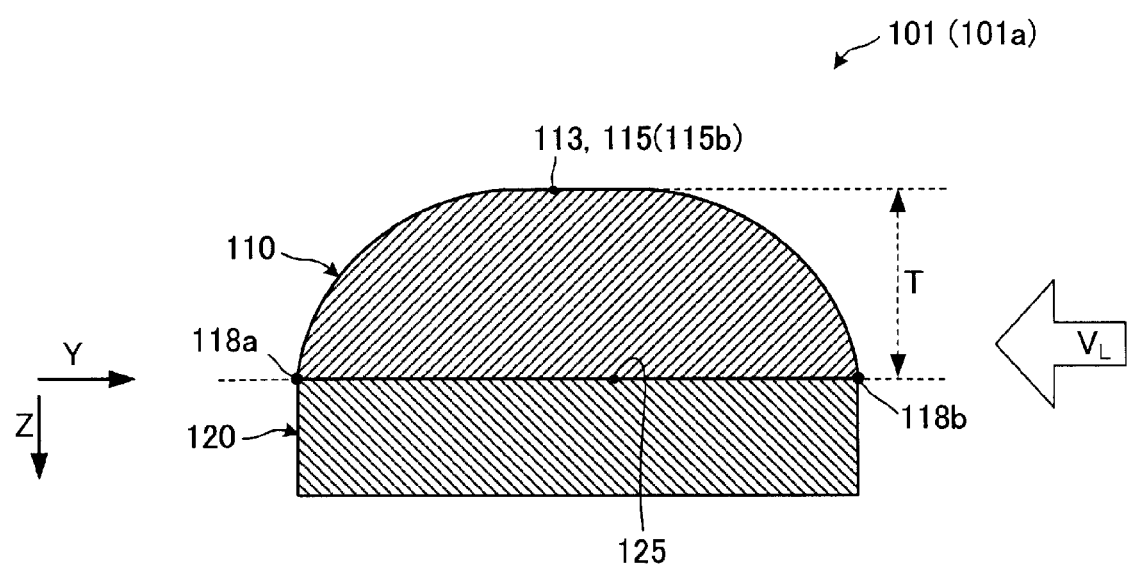
FIG. 7 is a schematic diagram of the A-A' cross section in FIG. 6A.

FIG. 7 is a schematic diagram of the A-A' cross section in FIG. 6A. This cross section corresponds to the cross section of the indication portion 115 taken perpendicularly to the detection surface 113 and along the extending direction of the indication portion 115. In this cross section, the portion other than both end portions 118a and 118b of the indication portion 115 projects out to the front side with respect to the reference line (the dashed line connecting between the end portion 118a and the end portion 118b in FIG. 7) connecting between both the end portions 118a and 118b of the indication portion 115. Since the indication portion 115 thus projects out to the front side, as shown in FIG. 6B, a part of the indication portion 115 is viewable as a surface also in the case where the inspection tool 101a for nucleic acid chromatography according to this embodiment is observed from the direction (for example, the side illustrated by the outlined arrows $V_L$ in FIG. 6A and FIG. 7) other than the front view. As a result, this allows simply determining the presence or absence of the indication (color) indicative of the detection of the target nucleic acid.

As shown in FIG. 7, in the inspection tool 101a for nucleic acid chromatography according to this embodiment, the porous sheet 110 has the shape (hog-backed shape) whose thickness is large in the center portion and decreases from the center portion toward both sides. The porous sheet 110 in this shape is brought into close contact with the flat attached surface 125, so as to form the shape where the detection surface 113 (and its partial region of the indication portion 115) in the porous sheet 110 project out to the front side.

In the inspection tool 101a for nucleic acid chromatography according to this embodiment, the detection surface 113 is preferred to project out to the front side with a curvature in the cross section perpendicular to the longitudinal direction of the porous sheet 110. As just described, in the case where the detection surface 113 projects out to the front side with the curvature, shading is less likely to occur on the detection surface 113 and the signal (color) appearing in the indication portion 115 becomes easily viewable. Here, "project out with the curvature" means that the detection surface of the porous sheet has an arc shape in the cross-sectional view.

Figure 8A:
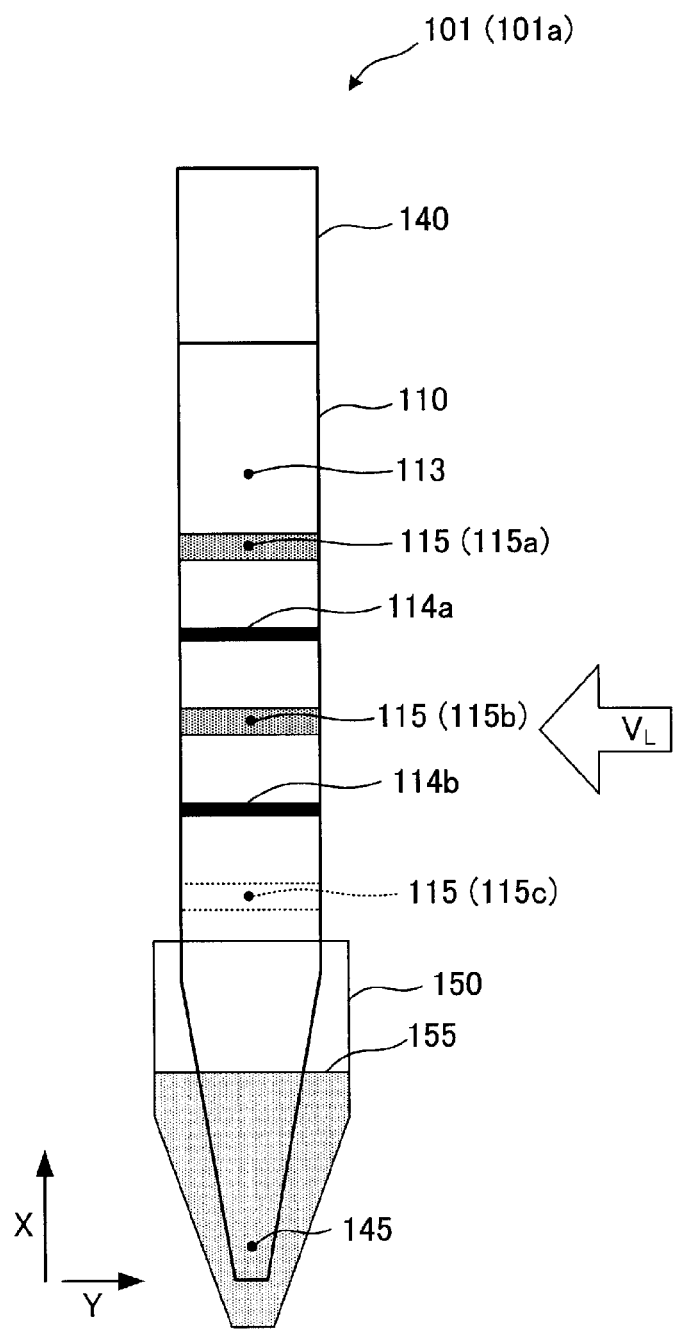
FIG. 8A is a front view schematically showing one mode of use of the inspection tool for nucleic acid chromatography shown in FIG. 6A.
Figure 8B:
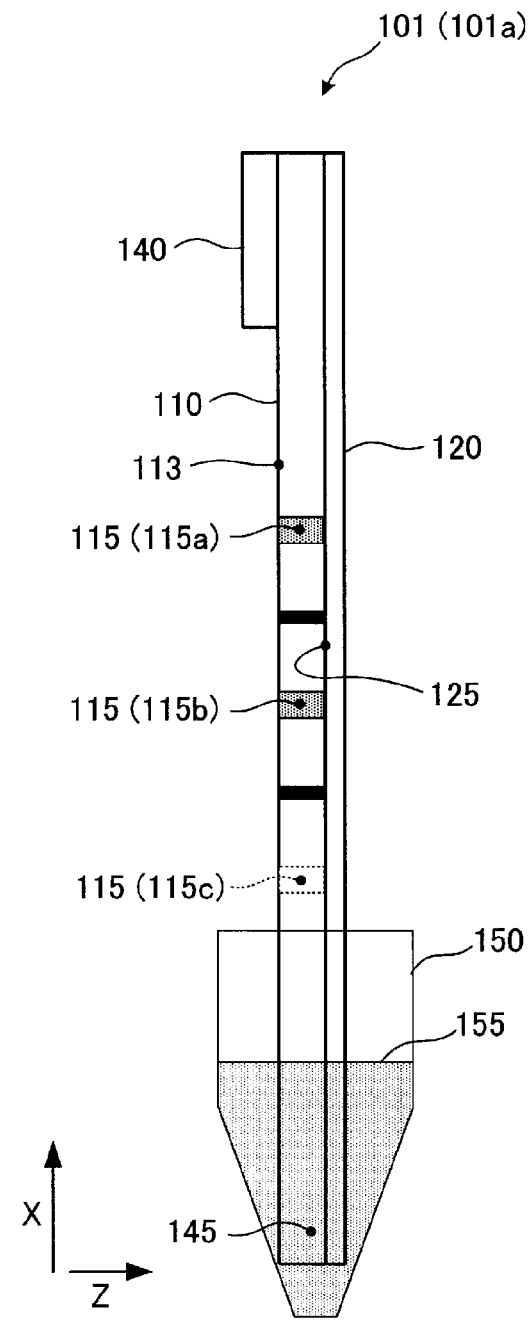
FIG. 8B is a side view schematically showing one mode of use of the inspection tool for nucleic acid chromatography viewed from the direction of an outlined arrow $V_L$ shown in FIG. 8A.

FIG. 8A and FIG. 8B are schematic diagrams showing one mode of use of the inspection tool 101a for nucleic acid chromatography shown in FIG. 6A. Here, FIG. 8A is a front view viewed from the same direction as that of FIG. 6A, and FIG. 8B is a side view viewed from the same direction as that of FIG. 6B. As shown in the drawing, the inspection tool 101a for nucleic acid chromatography according to this embodiment can be used such that, for example, a distal end portion 145 of the inspection tool 101a for nucleic acid chromatography is dipped in a liquid specimen 155 contained in a test tube 150. Thus, when the distal end portion 145 is dipped in the specimen 155, the specimen 155 expands within the porous sheet 110 due to a capillary action and is transported to another distal end portion (the distal end portion where the absorbent pad 140 is disposed). At this time, when the target nucleic acid is contained in the specimen 155, this target nucleic acid is captured by the nucleic acid probe fixed to the indication portion 115. As a result, the indication portion 115 is colored by the dye for labeling the target nucleic acid (see indication portions 115a and 115b in FIGS. 8A and 8B).

As shown in the drawing, in the inspection tool 101a for nucleic acid chromatography according to this embodiment, the detection surface 113 is partitioned into three areas along the longitudinal direction X by two position markers 114a and 114b. In these three areas, respective indication portions 115a to 115c are disposed one by one. To the indication portions 115a to 115c, respective nucleic acid probes are fixed to capture different types of target nucleic acid (target nucleic acids with different base sequences). For example, a nucleic acid probe for a target nucleic acid as a marker of an allergic disease is fixed to the indication portion 115a, a nucleic acid probe for a target nucleic acid as a tumor marker is fixed to the indication portion 115b, and a nucleic acid probe for a target nucleic acid as a marker of a viral infection is fixed to the indication portion 115c. This allows determining whether or not the person suffers from the above-described three types of diseases by one inspection. Assuming that this configuration is applied to the example shown in FIG. 8A and FIG. 8B, regarding the patient from which the specimen 155 is obtained in FIG. 8A and FIG. 8B, the colors are observed in the indication portions 115a and 115b while no color is observed in the indication portion 115c. Accordingly, the patient is determined to suffer from an allergic disease and a tumor but not to suffer from a viral infection.

In the inspection tool 101a for nucleic acid chromatography according to this embodiment, the indication portions 115a to 115c each extend in a straight line along the width direction Y perpendicular to the longitudinal direction X. In this embodiment, the indication portion 115 need not extend in a straight line along the width direction Y of the porous sheet 110. It is only necessary to dispose the indication portion so that the specimen 155 crosses the indication portion 115 in the course of expansion of the specimen 155 in the porous sheet 110. For example, the indication portion 115 can employ any shape such as a strip shape extending at an angle to intersect with the longitudinal direction X at 45 degrees and a meandering strip shape.

The inspection tool 101a for nucleic acid chromatography according to this embodiment includes the absorbent pad 140, which is in contact with a part of the porous sheet 110 and absorbs the specimen 155 having expanded in the porous sheet 110. In the case where the absorbent pad 140 is disposed like the inspection tool 101a for nucleic acid chromatography according to this embodiment, the absorbent pad 140 can absorb and hold the specimen 155 having expanded in the porous sheet 110. This allows increasing the liquid amount of the specimen 155 to expand in the porous sheet 110. Thus, this also allows increasing the amount of the target nucleic acid applied to the inspection tool 101a for nucleic acid chromatography. As a result, the amount of the target nucleic acid to be captured in the indication portion 115 is increased and the signal (color) indicative of the detection of the target nucleic acid appears to be thick. Thus, this configuration is preferred.

In the inspection tool 101a for nucleic acid chromatography according to this embodiment, all or a part of the target nucleic acid is prepared to have a single-stranded polynucleotide structure when the specimen 155 expands in the porous sheet 110. Additionally, the nucleic acid probe to be used at least partially has a single-stranded polynucleotide structure (a single-stranded polynucleotide with the base sequence complementary to the base sequence of the single-stranded polynucleotide of the target nucleic acid) that can be specifically hybridized with the single-stranded polynucleotide structure of the target nucleic acid. With use of these target nucleic acid and nucleic acid probe, when the target nucleic acid reaches the indication portion 115, the single-stranded polynucleotide structure of the target nucleic acid and the single-stranded polynucleotide structure of the nucleic acid probe are hybridized with each other (form a double strand). Then, the target nucleic acid is fixed to the indication portion 115 via the nucleic acid probe. Here, in the inspection tool 101a for nucleic acid chromatography according to this embodiment, the nucleic acid probe is not specifically limited and may be, for example, a DNA probe, an RNA probe, or Morpholino Antisense Oligo insofar as the nucleic acid probe has the single-stranded polynucleotide structure that can be specifically hybridized with the single-stranded polynucleotide structure of the target nucleic acid.

Additionally, the target nucleic acid can also employ a single-stranded DNA, a double-stranded DNA or RNA having an end portion in a single-stranded structure, and the like. A generally available method only needs to be applied to the labeling of the target nucleic acid. In the case where the target nucleic acid is prepared using the PCR method, it is possible to use a method for directly labeling a PCR product using at least one of dNTPs (dATP, dCTP, dGTP, and dTTP) labeled in advance as substrates for the polymerase reaction. Alternatively, it is possible to use a method for adding a label to a PCR product (double-stranded DNA) with no label afterward. The method for adding a label to a PCR product (double-stranded DNA) with no label afterward can employ, for example, a PCR primer that is modified such that both ends of the PCR product have single-stranded polynucleotide structures of specific base sequences. This modified PCR primer is used to obtain a PCR product, and the single-stranded polynucleotide structure of the obtained PCR product is hybridized with a labeled single-stranded polynucleotide having the base sequence complementary to this structure. With this hybridization, the target nucleic acid (PCR product) can be labeled.

In the inspection tool 101a for nucleic acid chromatography according to this embodiment, the porous sheet 110 can employ a sheet with countless pores made of nitrocellulose, cellulose, polyethersulfone, nylon, PVDF, and the like.

Figure 9:
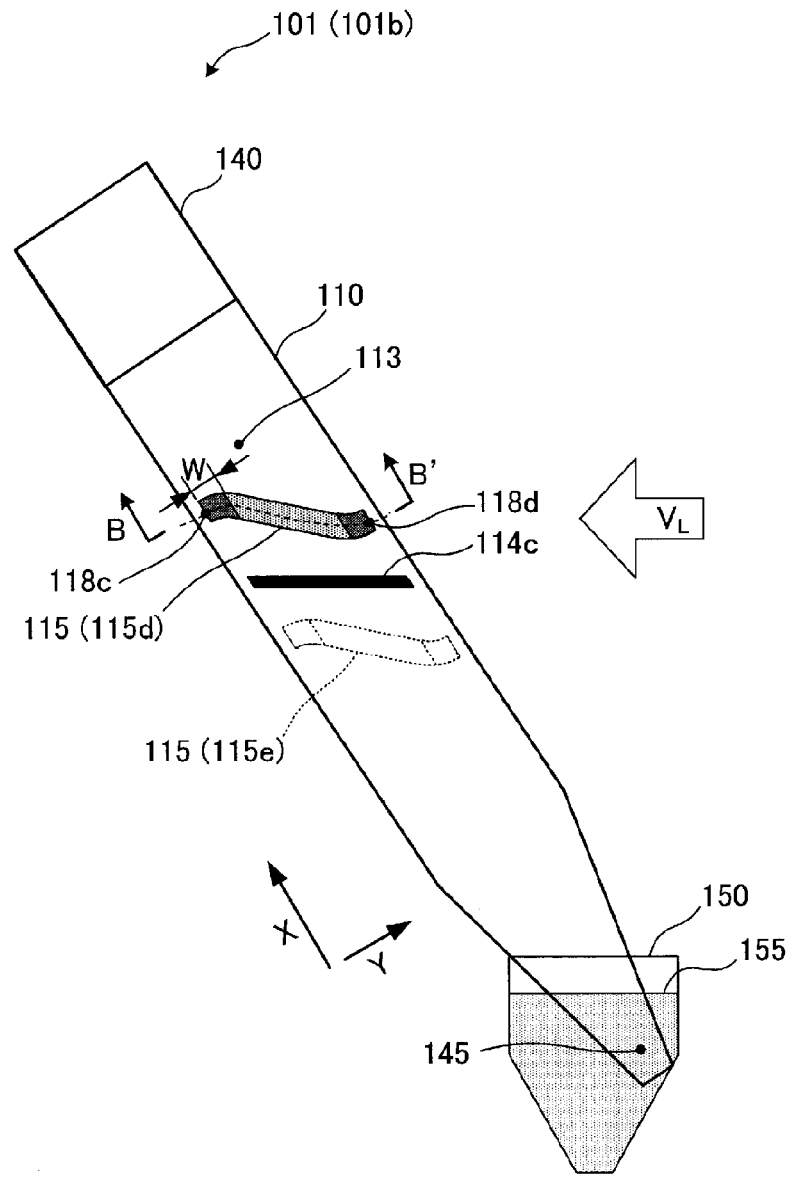
FIG. 9 is a front view schematically showing another embodiment of the inspection tool for nucleic acid chromatography according to the second invention.

FIG. 9 is a front view schematically showing another embodiment of the inspection tool for nucleic acid chromatography according to the second invention. As shown in the drawing, in an inspection tool 101b for nucleic acid chromatography according to this embodiment, indication portions 115d and 115e are bent in an S shape, and both end portions 118c and 118d of the indication portions 115d and 115e do not reach the side edges of the detection surface 113.

Figure 10:
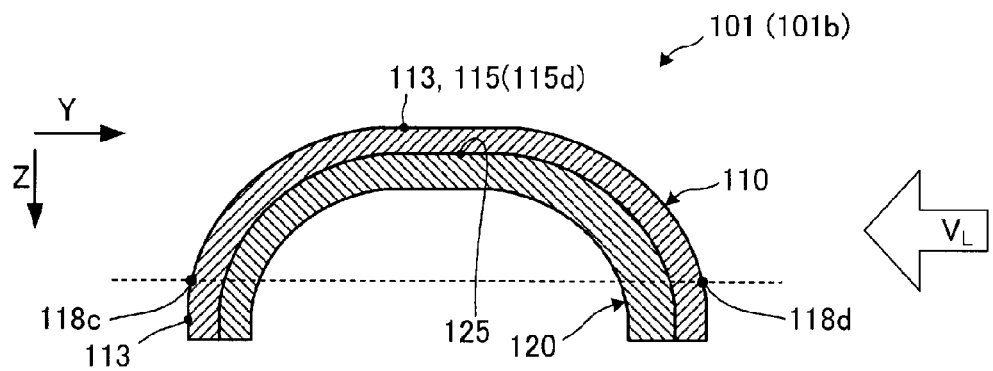
FIG. 10 is a schematic diagram of the B-B' cross section in FIG. 9.

FIG. 10 is a schematic diagram of the B-B' cross section in FIG. 9. This cross section includes the center line of the indication portion 115d as illustrated by the dashed line connecting between both the end portions 118c and 118d of the strip-shaped indication portion 115d in FIG. 9. As shown in the drawing, in the inspection tool 101b for nucleic acid chromatography according to this embodiment, the top surface of the sheet-shaped backing member 120 curved in an arch shape is defined as the attached surface 125. To this attached surface 125, the porous sheet 110 with a uniform thickness is attached. Accordingly, in this cross section, the portion other than both the end portions 118c and 118d of the indication portion 115d projects out to the front side with respect to the reference line (the dashed line in FIG. 10) connecting between both the end portions 118c and 118d of the indication portion 115d.

Figure 11:
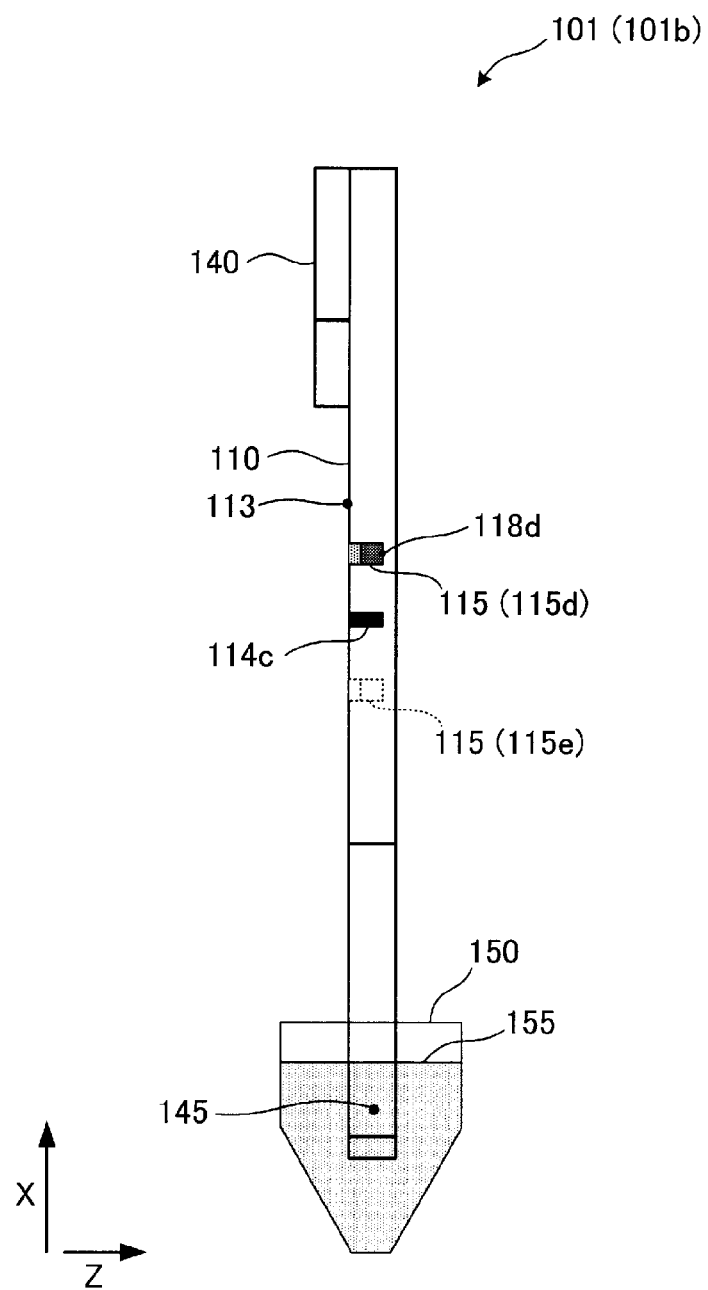
FIG. 11 is a schematic side view of the inspection tool for nucleic acid chromatography viewed from the direction shown by an outlined arrow $V_L$ in FIG. 9.

FIG. 11 is a side view of the inspection tool 101b for nucleic acid chromatography viewed from the direction shown by an outlined arrow $V_L$ in FIG. 9 and FIG. 10. As described above, the indication portion 115d project out to the front side. Accordingly, a part of the indication portion 115d is viewable as a surface also in the case where the inspection tool 101b for nucleic acid chromatography according to this embodiment is observed from the direction other than the front view. As a result, this allows simply determining the presence or absence of the indication (color) indicative of the detection of the target nucleic acid in the indication portion 115d.

Further, as shown in FIG. 9, in the inspection tool 101b for nucleic acid chromatography according to this embodiment, in the indication portion 115 (the indication portions 115d and 115e), the nucleic acid probe is fixed at a higher density in the respective regions having a predetermined width W from both the end portions 118c and 118d toward the center in the indication portion 115 compared with in the residual region in the same indication portion 115. In FIG. 9 and FIG. 11, the gradation of density of the nucleic acid probe is shown by the thickness of the hatching on the indication portion 115d. As just described, when the nucleic acid probe is fixed at a high density in the region in the vicinity of both the end portions 118c and lied of the indication portion 115, the signal (color) indicative of the detection of the target nucleic acid appears to be thick in the region in the vicinity of both the end portions 118c and 118d of the indication portion 115. As a result, as shown in FIG. 11, in the case where the inspection tool 101b for nucleic acid chromatography is observed from the side, the presence of the signal (color) indicative of the detection of the target nucleic acid can be simply determined even when only the region in the vicinity of the end portion 118d of the indication portion 115 is visible. Assuming that this configuration is applied to the example shown in FIG. 11, also in the case where the inspection tool 101b for nucleic acid chromatography is observed from the side, it is possible to simply determine that the signal (color) indicative of the detection of the target nucleic acid occurs in the indication portion 115d while the signal (color) does not occur in the indication portion 115e. In particular, in the inspection tool 101b for nucleic acid chromatography according to this embodiment, the detection of the target nucleic acid is supposed to produce a thick color in the vicinity of the end portion 118d of the indication portion 115. Accordingly, when the color is recognized in the vicinity of the end portion 118d of the indication portion 115 in the side view, it is possible to determine that the target nucleic acid is not detected without hesitation. That is, the inspection tool 101b for nucleic acid chromatography according to this embodiment allows quickly determining the presence or absence of the target nucleic acid.

In the inspection tool 101 for nucleic acid chromatography according to the second invention, in the respective regions with the predetermined width W from both the end portions 118c and 118d toward the center in the indication portion 115, the average aperture diameter of the porous sheet 110 is preferred to be smaller than that of the residual region in the same indication portion 115. As just described, in the case where the average aperture diameter of the porous sheet 110 is small in the regions in the vicinity of both the end portions 118c and 118d of the indication portion 115, the target nucleic acids are captured in a densely gathered state in these regions in the vicinity of both the end portions 118c and 118d. As a result, the signal (color) indicative of the detection of the target nucleic acid appears to be thick. Thus, this configuration is preferred.

Here, in the inspection tool 101 for nucleic acid chromatography according to the second invention, in some cases, the nucleic acid probe is fixed at a high concentration in the regions in the vicinity of both the end portions 118c and 118d of the indication portion 115 and the average aperture diameter of the porous sheet 110 is small in the regions in the vicinity of both the end portions 118c and 118d of the indication portion 115. In this case, the region where the nucleic acid probe is fixed at the high concentration and the region where the average aperture diameter of the porous sheet 110 is small need not completely coincide with each other.

Regarding the porous sheet 110, to prepare the porous sheet 110 where the respective regions with the predetermined width W from both the end portions 118c and 118d toward the center in the indication portion 115 have average aperture diameters smaller than that of the residual region in the same indication portion 115, the following process is preferred. Firstly, to form the porous sheet 110 in an elongated shape, it is preferred to compress both the side edges (both the side edges in the width direction Y) (alternatively, both the side edges and the portion in the vicinity of the side edges) of the porous sheet 110 and then cut the porous sheet 110. Alternatively, it is preferred to use a method in which cutting is performed while compressing. As just described, compressing both the side edges during cutting of the porous sheet 110 allows decreasing the average aperture diameter of the porous sheet 110 in the portion at the periphery of both the side edges of the porous sheet 110. Specifically, it is preferred to use a method for cutting both the side edges of the porous sheet 110 using a push cutter with a dull blade edge and the like.

EXAMPLES

The following describes the present invention further in detail based on Examples. The present invention is not limited to these Examples.

[Preparation of Inspection Tool for Nucleic Acid Chromatography]

Merck Millipore Hi-Flow Plus membrane sheets (hereinafter referred to as the "porous sheet") (45 mm×300 mm) were attached to Merck Millipore laminated, membrane cards (hereinafter referred to as "the backing member") (60 mm×300 mm) so as to prepare composite sheets. Subsequently, according to the following procedures 1 to 7, capture DNA probe solutions including the base sequences shown in Table 1 were spotted on the surfaces of the porous sheets of the composite sheets using an NGK Insulators, Ltd. GENESHOT (Registered trademark) spotter, so as to fix capture DNA probes to the porous sheet surfaces. Subsequently, the composite sheet was processed by being cut into an elongated shape, so as to obtain a strip of an inspection tool for nucleic acid chromatography. Here, the GENESHOT (R) spotter is the device using a discharge unit (inkjet method) disclosed in JP-A-2003-75305.

[Procedure 1: Preparation of Capture DNA Probe Solution]

Nine types of capture DNA probes were synthesized in accordance with the base sequences in Table 1. Water solutions where these capture DNA probes were dissolved by Tris-EDTA buffer were mixed with SSC buffer solution and bromophenol blue (BPB), so as to prepare solutions with 0.05 wt % of bromophenol blue and 2 to 60 µM of a capture DNA probe concentration.

TABLE 1

| Probe Number | Sequence (5' to 3') |
|---|---|
| 1 | TGTTCTCTGACCAATGAATCTGC |
| 2 | TGGAACTGGGAACGCTTTAGATG |
| 3 | TTCGCTTCGTTGTAATTTCGGAC |
| 4 | AGGCATCCTAAGAAATCGCTACT |
| 5 | TAGCCCAGTGATTTATGACATGC |
| 6 | AGGTCCGGTAGTAATTTAGGTGC |
| 7 | TATTCTACCAACGACATCACTGC |
| 8 | CATCTCCAAGAATTGACCCACCA |
| 9 | GAAGGATCGCTTTTATCTGGCAT |

[Procedure 2: Examination on Spotting Conditions]

Before spotting on the surface of the porous sheet of the composite sheet, check spotting was performed on a checking sheet to examine the spotting conditions. Specifically, the capture DNA probe solution was injected into the liquid injection block arranged in the discharge unit of the GENE-SHOT (R) spotter to perform the check spotting on the checking sheet. The quality was checked on the checking sheet regarding five points of: (i) whether there is no defective formation of the spots; (ii) whether the spots do not have irregular shapes; (iii) whether the spot diameter is not shifted by 10% or more with respect to the designed value; (iv) whether there is no occurrence of unnecessary spots (the spots typically referred to as "satellites"); and (v) whether the spot position is not shifted by one-third or more of the spot diameter. Since the capture DNA probe solution was colored in blue by bromophenol blue, it was possible to check the spots on the checking sheet by visual observation for the above-described points (i) to (v).

As a result of the above-described quality checking, when a failure is detected in the check spotting, the drive signal for the piezoelectric/electrostrictive device disposed in the discharge unit was adjusted to perform check spotting again. The drive signal was adjusted by changing the voltage value, the rising time up to a predetermined voltage, the keeping time of the predetermined voltage value, and the voltage falling time. When the failure was still detected, the check spotting was performed after the capture DNA probe solution was removed from the discharge unit by vacuum suction and the capture DNA probe solution was again injected into the liquid injection block. The above-described operation was repeated until a failure spot was not detected.

[Procedure 3: Spotting of Capture DNA Probe Solution]

After confirming that the failure spot was not detected, the capture DNA probe was spotted on the surface of the porous sheet of the composite sheet using the following method. Firstly, one type of the capture DNA probe solution was spotted in a state where the discharge unit and the porous sheet were not in contact with each other, such that: the pitch of spots was set to 0.05 mm both in the lateral direction [corresponding to "the width direction Y" of a completed product] and in the longitudinal direction [corresponding to "the longitudinal direction X" of the completed product]; and the spots were arranged in a straight line in the lateral direction and the longitudinal direction on the surface of the porous sheet. Accordingly, the line (corresponding to "the indication portion" of the completed product) having 300 mm in the lateral direction and 0.5 mm in the longitudinal direction was formed on the surface of the porous sheet of the composite sheet. Specifically, on the porous sheet, the discharge unit was moved in a straight line along the lateral direction [corresponding to "the width direction Y" of the completed product] of the composite sheet. When the discharge unit reaches the ending point, the composite sheet was moved by one row or a plurality of rows in the longitudinal direction [corresponding to "the longitudinal direction X" of the completed product]. Subsequently, the discharge unit was again moved in a straight line along the lateral direction [corresponding to "the width direction Y" of the completed product] of the composite sheet. With these procedures, the line (corresponding to "the indication portion" of the completed product) was formed.

Before the spot of the capture DNA probe discharged from the discharge unit hits and this spot is dried, when the next adjacent spot hits and both the spots have contact with each other, bleeding and color unevenness may occur. Therefore, firstly, the anterior half of spotting was performed at a pitch of 0.1 mm in the lateral direction [corresponding to "the width direction Y" of the completed product]. Subsequently, in the mode where a new spot of the capture DNA probe was hit against the clearance between the spots, the posterior half of the spotting was performed at a pitch of 0.1 mm. As just described, formation of the spot rows at the pitch of 0.05 mm by spotting separately in the anterior half and the posterior half allowed preventing bleeding and color unevenness.

Figure 12:
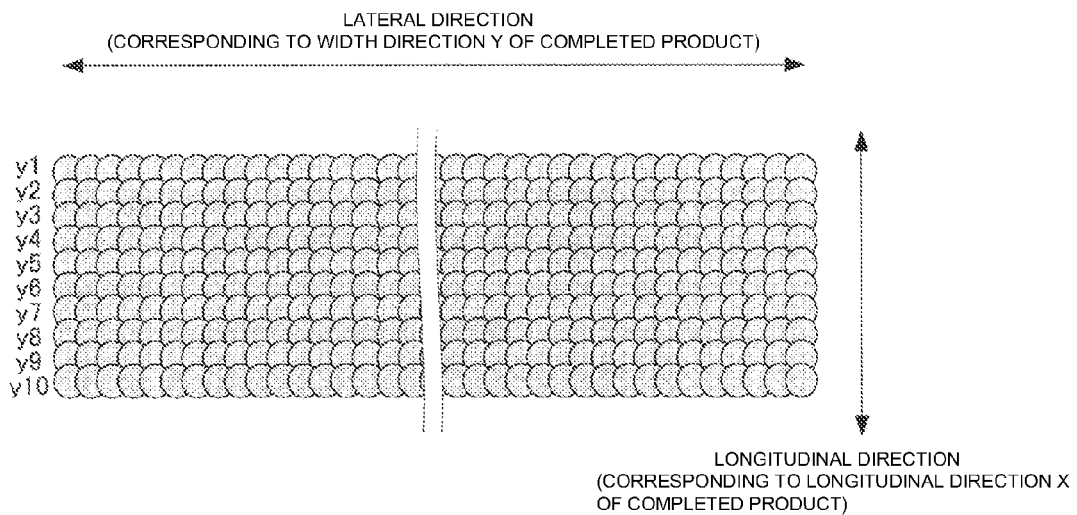
FIG. 12 is an explanatory diagram showing the outline of spotting of capture DNA probe solutions.

As shown in FIG. 12, the above-described line with the length of 300 mm× the width of 0.5 mm is formed of spot rows of y1 to y10, which are arranged in the line longitudinal direction [corresponding to "the longitudinal direction X" of the completed product]. The line with the length of 300 mm× the width of 0.5 mm can be formed by forming spot rows in the order corresponding to y1, y2, y3, y4, y5, y6, y7, y8, y9, and y10. When the subsequent spot row overlaps with the prior spot row before the prior spot row is dried, bleeding and color unevenness may occur in this overlapped portion. Therefore, spotting in the order corresponding to y1, y10, y2, y9, y3, y8, y4, y7, y5, and y6 allows avoiding the situation where the subsequent spot row overlaps with the prior spot row before the prior spot row is dried. As a result, this made it possible to inhibit the occurrence of bleeding while setting the line width within a range of 0.45 to 0.55 mm (the designed value of 0.50 mm ± the error of 0.05 mm). Furthermore, like spotting in the order corresponding to y1, y6, y2, y7, y3, y8, y4, y9, y5, and y10 or in the order corresponding to y1, y3, y5, y7, y9, y2, y4, y6, y8, and y10, spotting not to form adjacent spot rows in series allowed preventing color unevenness in the line in addition to setting the line width due to bleeding within the range of 0.45 mm to 0.55 mm (the designed value of 0.50 mm ± the error of 0.05 mm).

Finally, on the surface of the porous sheet of the composite sheet, nine lines each (with an error of 0.1 mm or less with respect to the designed value of the line width) with a length of 300 mm× a width of 0.5 mm were formed at a pitch of 1.2 mm in the longitudinal direction [corresponding to "the longitudinal direction X" of the completed product]. These nine lines were formed as capture DNA probes (of probe numbers 1 to 9 in Table 1) of mutually different types. That is, the respective nine types of capture DNA probes (of the probe numbers 1 to 9) were fixed to different positions on the surface of the porous sheet.

[Procedure 4: Spotting of Position Marker Line]

To facilitate determination of the position of the indication portion, a liquid containing pigment-based magenta ink was spotted so as to form lines of the position marker.

Figure 13:
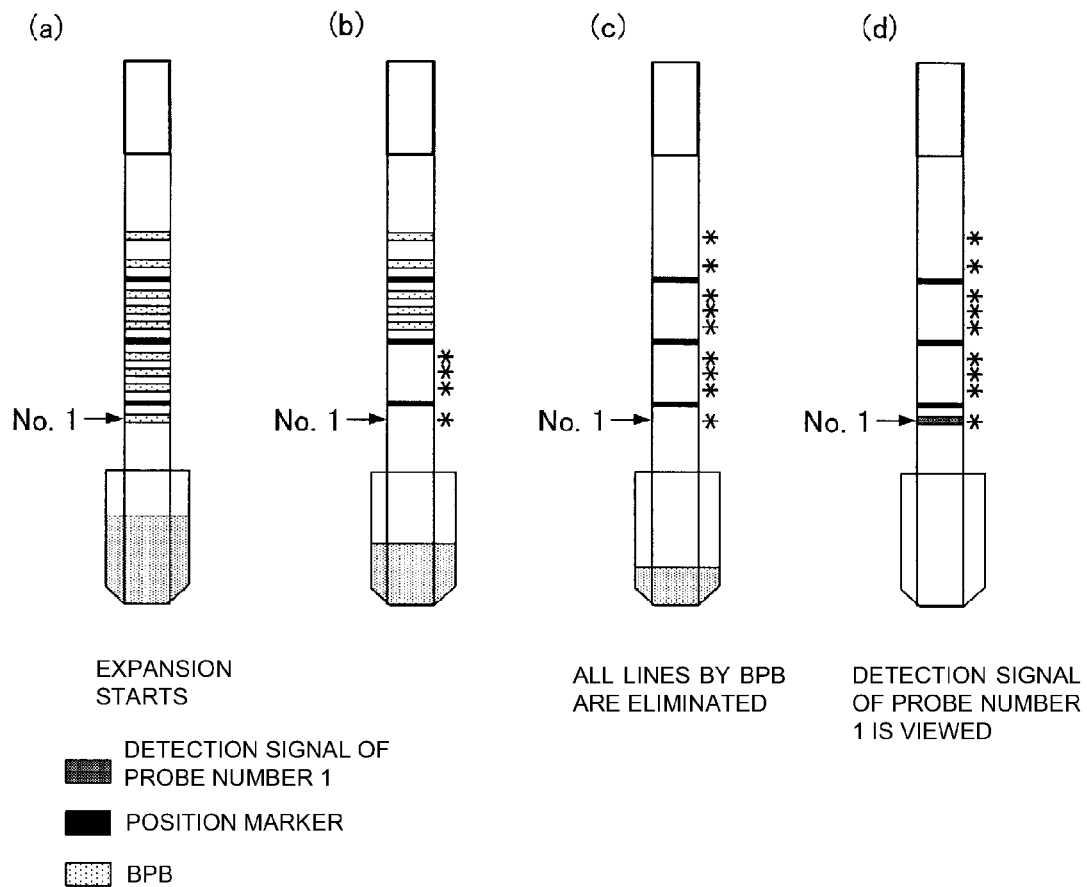
FIG. 13 is an explanatory diagram of an expansion process and a detection process.

Here, the lines of the position marker were formed by spotting with a method similar to that of the spotting of the capture DNA probe solution. As a result, a composite sheet (see FIG. 13 (a), which shows a completed product obtained by processing this composite sheet) was obtained. In the composite sheet, the nine lines [colored by bromophenol blue (BPB)] of the capture DNA probe and three lines (colored by the pigment-based magenta ink) of the position marker were arranged in a striped pattern.

[Procedure 5: Fixing of Capture DNA]

After the completion of formation of the lines of the capture DNA probe and the lines of the position marker through the procedure 4, the composite sheet was heated at 50° C. for 30 minutes to fix the capture DNA probes to the surface of the porous sheet, so as to fix the pigment-based magenta ink of the position marker to the surface of the porous sheet.

[Procedure 6: Checking]

The porous sheet of the composite sheet was checked regarding the points [(i) to (v)] similar to checking in the above-described procedure 3.

[Procedure 7: Processing]

Examples 1 to 5

After checking in the procedure 6, the composite sheets without abnormality were processed with any method of the following processing methods 1 to 3 to prepare strips of the inspection tools for nucleic acid chromatography in arched shapes along the longitudinal direction such that the depression values of the porous sheets had 1.0 mm (Example 1), 2.0 mm (Example 2), 3.0 mm (Example 3), 4.0 mm (Example 4), and 5.0 mm (Example 5) (see the value of D in FIG. 4 for "the depression values of the porous sheets")

[Processing Method 1]

A Merck Millipore absorbent pad (20 mm×300 mm) was mounted on the porous sheet to cover about 5 mm. To fix the absorbent pad, after an adhesive tape (25 mm×300 mm) was attached to the top surface portion of the absorbent pad in advance, the protruding portion of the adhesive tape was attached to the porous sheet while the protruding portion of the adhesive tape was pulled in the longitudinal direction (corresponding to "the longitudinal direction X" of the completed product) of the composite sheet. This method provided a composite sheet with arched porous sheet and arched backing member for backing this porous sheet (see FIG. 4 for the arched shape). Subsequently, this composite sheet was cut using a cutting machine or a guillotine cutter so as to obtain 85 strips (the inspection tools for nucleic acid chromatography) each with a width of 3.5 mm and a length of 60 mm (a length of 45 mm for the porous sheet). Here, the depression value of the porous sheet was 1.0 to 5.0 mm.

[Processing Method 2]

A Merck Millipore absorbent pad (20 mm×300 mm) was mounted on the porous sheet to cover about 5 mm. To fix the absorbent pad, an adhesive tape (25 mm×300 mm) was attached to the porous sheet. A fixture adjusted such that the depression value of the porous sheet was set to 1.0 to 5.0 mm was prepared so as to fix the composite sheet to this fixture. In this fixed state, the composite sheet was cut using a cutting machine or a guillotine cutter so as to obtain 85 strips (the inspection tools for nucleic acid chromatography) each with a width of 3.5 mm and a length of 60 mm (a length of 45 mm for the porous sheet).

[Processing Method 3]

A Merck Millipore absorbent pad (20 mm×300 mm) was mounted on the porous sheet to cover about 5 mm. To fix the absorbent pad, an adhesive tape (25 mm×300 mm) was attached to the porous sheet. The composite sheet was cut using a cutting machine or a guillotine cutter so as to obtain 85 strips each with a width of 3.5 mm and a length of 60 mm (a length of 45 mm for the porous sheet). Subsequently, an appropriate stress was applied to one distal end portion or both distal end portions of these strips to arch the strips such that the depression values of the porous sheets had 1.0 to 5.0 mm, so as to obtain the strips of the inspection tools for nucleic acid chromatography.

Comparative Example 1

[Processing Method 4]

A Merck Millipore absorbent pad (20 mm×300 mm) was mounted on the porous sheet to cover about 5 mm. To fix the absorbent pad, an adhesive tape (25 mm×300 mm) was attached to the porous sheet. The composite sheet was cut using a cutting machine or a guillotine cutter so as to obtain 85 strips (the inspection tools for nucleic acid chromatography) each with a width of 3.5 mm and a length of 60 mm (a length of 45 mm for the porous sheet). Here, the obtained strips of the inspection tools for nucleic acid chromatography had flat porous sheets, that is, depression values of 0.0 mm for the porous sheets.

Examples 6 to 10

After checking in the procedure 6, the composite sheets without abnormality were processed with the following processing method 5 or processing method 6 to prepare strips of the inspection tools for nucleic acid chromatography such that the differences in height (protrusion value) between the center portion and the edge portion in the porous sheets were 0.01 mm (Example 6), 0.03 mm (Example 7), 0.05 mm (Example 8), 0.07 mm (Example 9), and 0.10 mm (Example 10). Here, the above-described difference in height (protrusion values) is the distance from the reference line connecting the surfaces of both the end portions of the porous sheet to the surface of the center portion of the porous sheet with reference to "the protrusion value T" in FIG. 7.

[Processing Method 5]

A Merck Millipore absorbent pad (20 mm×300 mm) was mounted on the porous sheet to cover about 5 mm. To fix the absorbent pad, an adhesive tape (25 mm×300 mm) was attached to a membrane plate. Subsequently, when the composite sheet was processed using a cutting machine, the blade of the cutting machine is brought into contact with the surface of the porous sheet and then the blade was pressed into the porous sheet so as to cut the composite sheet. This allowed obtaining strips of the inspection tools for nucleic acid chromatography such that the thickness of the center portion was 0.55 mm and the thickness in both the edge portions was 0.45 mm in the porous sheet. That is, a hog-backed shape, where the center portion projects with respect to both the end portions by 0.10 mm in the porous sheet, was provided. Similar work was repeated so as to obtain 85 strips each with a width of 3.5 mm and a length of 60 mm (a length of 45 mm for the porous sheet) from one composite sheet. Furthermore, the force for pressing into the blade of the cutting machine was adjusted to also prepare strips with porous sheets where the differences in height (protrusion values) between the center portion and the edge portion were 0.01 mm, 0.03 mm, 0.05 mm, and 0.07 mm other than 0.10 mm described above.

[Processing Method 6]

A Merck Millipore absorbent pad (20 mm×300 mm) was mounted on the porous sheet to cover about 5 mm. To fix the absorbent pad, an adhesive tape (25 mm×300 mm) was attached to a membrane plate. Subsequently, when the composite sheet was processed, the porous sheet was pressed and cut by a cutter with a flat blade edge, not with an sharply-angled blade edge using a cutting machine or a guillotine cutter so as to cut the composite sheet. Furthermore, an adhesive agent was applied to the blade edge so as to more reliably press and cut the porous sheet. This allowed obtaining strips with the porous sheets in the hog-backed shapes where the center portion projects with respect to both the end portions in the porous sheets such that the differences in height (protrusion values) between the center portion and the edge portion in the porous sheets were 0.01 mm, 0.03 mm, 0.05 mm, 0.07 mm, and 0.10 mm. Here, 85 strips each with a width of 3.5 mm, a length of 60 mm (a length of 45 mm for the porous sheet) were obtained from one composite sheet.

Comparative Example 2

[Processing Method 7]

A Merck Millipore absorbent pad (20 mm×300 mm) was mounted on the porous sheet to cover about 5 mm. To fix the absorbent pad, an adhesive tape (25 mm×300 mm) was attached to a membrane plate. Cutting using a keen blade with a sharp blade edge allowed obtaining strips of the inspection tools for nucleic acid chromatography such that the thickness of the porous sheet was uniform (0.55 mm) and the difference in height (protrusion value) between the center portion and both the sides in the porous sheet was 0.00 mm.

[Evaluation Test]

The strips of the inspection tools for nucleic acid chromatography in Examples 1 to 10 and Comparative Examples 1 and 2 were evaluated using a chromatography method in accordance with the following procedures 8 to 10.

[Procedure 8: Preparation of Mobile Phase]

A sample DNA (here, modified with an amino group) with the base sequence complementary to the base sequence of the probe number 1 was fixed to a carboxylated latex particle (with a color of blue and an average particle diameter of 400 nm). The latex particles to which these sample DNAs were fixed were dispersed in sterile water as the mobile phase.

[Procedure 9: Expansion Process]

To a microtube with 0.2 ml, 50 µl of the mobile phase was dispensed. Then, the distal end of the strip of the inspection tool for nucleic acid chromatography was immersed in the mobile phase. Immediately after the immersion, the mobile phase moved upward (the direction to the other distal end where the absorbent pad was disposed) in the porous sheet by a capillary action. Bromophenol blue (BPB) was not fixed to the porous sheet, and was thus washed away by the mobile phase. This washing eliminates the lines by bromophenol blue [in FIGS. 13(b) to 13(d), the eliminated lines are illustrated by asterisks (*)]. Thus, as the mobile phase moves upward, nine lines by bromophenol blue were sequentially eliminated. This allowed simply checking which position the mobile phase had reached in the porous sheet. Here, since the pigment-based magenta ink of the position marker was fixed to the porous sheet and was insoluble in the mobile phase, the pigment-based magenta ink was not washed away by the mobile phase.

[Procedure 10: Detection Process]

Since the sample DNA in the mobile phase has the base sequence complementary to the capture DNA probe of the probe number 1, the sample DNA binds specifically with the capture DNA probe of the probe number 1 by hybridization reaction. Accordingly, the latex particle to which the sample DNA is fixed is captured by the capture DNA probe of the probe number 1. In the indication portions to which the capture DNA probes of the probe number 1 were fixed, the latex particles were accumulated, aggregated, and then colored in blue [see FIG. 13(d)] in association with the progress of the hybridization reaction between the sample DNA and the capture DNA probe of the probe number 1. About 20 minutes after the immersion in the mobile phase, all of the mobile phase moved to the absorbent pad and then the reaction completed. As described in the above-described procedure 9 and procedure 10, the colors of the lines by bromophenol blue (EPB) were once eliminated in association with expansion (elevation) of the mobile phase [with reference to FIG. 13 (c)]. Then, the indication portion of the probe number 1 was colored (in blue) by accumulation of the latex particles [with reference to FIG. 13 (d)]

[Result of Evaluation Test]

Regarding the strips of the inspection tools for nucleic acid chromatography in Examples 1 to 5 and Comparative Example 1, the evaluation results are shown in Table 2.

TABLE 2

|  | Depression Value (mm) | Handling | Color of Indication Portion | Absorption of Mobile Phase |
| --- | --- | --- | --- | --- |
| Example 1 | 1.0 | Good | Excellent | Excellent |
| Example 2 | 2.0 | Excellent | Excellent | Excellent |
| Example 3 | 3.0 | Excellent | Excellent | Excellent |
| Example 4 | 4.0 | Excellent | Excellent | Excellent |
| Example 5 | 5.0 | Excellent | Good | Good |
| Comparative Example 1 | 0.0 | Failure | Failure | Excellent |

(Handling)

As shown in Table 2, in Example 1 where the depression value of the porous sheet was 1.0 mm, the handling took a little time when the strip was placed on a flat desk or taken out from the packing case [the evaluation result was good indicated as "Good" in Table 2]. In Examples 2 to 5 where the depression value of the porous sheet was 2.0 to 5.0 mm, the handling was really excellent [the evaluation result was excellent indicated as "Excellent" in Table 2]. In contrast, in Comparative Example 1 where the depression value of the porous sheet was 0.00 mm, the handling was difficult when the strip was placed on a flat desk or taken out from the packing case. Accordingly, in Comparative Example 1, the region where the capture DNA probes were spotted was touched by hand or the strip was deformed in some cases [the evaluation result was poor indicated as "Failure" in Table 2]

(Color of Indication Portion)

Regarding the color of the indication portion where the capture DNA probe of the probe number 1 was fixed, in Examples 1 to 4 where the depression value of the porous sheet was 1.0 to 4.0 mm, it was observed that the color of the indication portion was considerably thick (thicker than that at an ordinary level) as the depression value increased [the evaluation result was excellent indicated as "Excellent" in Table 2]. In the strip of the inspection tool for nucleic acid chromatography in Example 5, it was sometimes impossible to expand the total amount of the mobile phase (described in detail below). In this case, the color of the indication portion was thick as an ordinary level [the evaluation result was good indicated as "Good" in Table 2]. Here, in Comparative Example 1 where the depression value of the porous sheet was 0.0 mm, the color of the indication portion was thin and blur [the evaluation result was poor indicated as "Failure" in Table 2]

(Absorption of Mobile Phase)

In the strips of the inspection tools for nucleic acid chromatography in Examples 1 to 4 and Comparative Example 1, it was possible to move the total amount of the mobile phase in the microtube to the absorbent pad [the evaluation result was excellent indicated as "Excellent" in Table 2]. In the strip of the inspection tool for nucleic acid chromatography in Example 5, since the absorbent pad was partially delaminated and a gap occurred between the porous sheet and the absorbent pad, it was sometimes impossible to move approximately the total amount of the mobile phase to the absorbent pad [the evaluation result was good indicated as "Good" in Table 2].

Thus, in the strips of the inspection tools for nucleic acid chromatography in Examples 1 to 5, it was found that all points of "handling," "color of indication portion," and "absorption of mobile phase" were preferable (had the evaluation result of "good" or better result).

Regarding the strips of the inspection tools for nucleic acid chromatography in Examples 6 to 10 and Comparative Example 2, the evaluation results are shown in Table 3.

TABLE 3

|  | Protrusion Value (mm) | Visibility from Side | Ease of Determination of Color of Indication Portion from Side |
|---|---|---|---|
| Example 6 | 0.01 | Good | Good |
| Example 7 | 0.03 | Excellent | Good |
| Example 8 | 0.05 | Excellent | Good |
| Example 9 | 0.07 | Excellent | Excellent |
| Example 10 | 0.10 | Excellent | Excellent |
| Comparative Example 2 | 0.00 | Failure | Failure |

(Visibility from Side)

As shown in Table 3, in the case where the difference in height (protrusion value) between the center portion and the end portions in the porous sheet was 0.01 mm like Example 6, it was possible to barely view the line of the position marker from the side of the strip of the inspection tool far nucleic acid chromatography [the evaluation result was good indicated as "Good" in Table 3]. Furthermore, in the case where the difference in height (protrusion value) between the center portion and the end portion in the porous sheet was 0.03 to 0.10 mm like Examples 7 to 10, it was possible to clearly view the line of the position marker [the evaluation result was excellent indicated as "Excellent" in Table 3]. Additionally, in the case where the difference in height (protrusion value) between the center portion and the end portions in the porous sheet was 0.03 to 0.10 mm like Examples 7 to 10, it was found that the visibility of the line of the position marker increased as the difference in height between the center portion and the end portions in the porous sheet increased. In contrast, in the case where the difference in height (protrusion value) between the center portion and the end portions in the porous sheet was 0.00 mm like Comparative Example 2, it was impossible to view the line of the position marker from the side of the strip of the inspection tool for nucleic acid chromatography [the evaluation result was poor indicated as "Failure" in Table 3].

(Ease of Determination of Color of Indication Portion from Side)

In the case where the difference in height (protrusion value) (difference in thickness) between the center portion and the end portions in the porous sheet was 0.01 to 0.05 mm like Examples 6 to 8, it was possible to check the color of the indication portion from the side of the strip of the inspection tool for nucleic acid chromatography [the evaluation result was good indicated as "Good" in Table 3]. Furthermore, in the case where the difference in height (protrusion value) (difference in thickness) between the center portion and the end portions in the porous sheet was 0.07 to 0.10 mm like Examples 9 and 10, it was possible to very clearly check the color of the indication portion from the side of the strip of the inspection tool for nucleic acid chromatography [the evaluation result was excellent indicated as "Excellent" in Table 3]. In contrast, the difference in height (protrusion value) (difference in thickness) between the center portion and the end portions in the porous sheet was 0.00 mm like Comparative Example 2, it was impossible to check the color of the indication portion from the side of the strip of the inspection tool for nucleic acid chromatography [the evaluation result was poor indicated as "Failure" in Table 3].

Here, the results of microscope observation and the like for the porous sheet surfaces in the strips of the inspection tools for nucleic acid chromatography in Examples 6 to 10 and Comparative Example 2 were taken into consideration. It was found that when a membrane plate (porous sheet) where the original thickness was uniform was used as the material and the porous sheet was processed such that the center portion was thick and both the edge portions were thin in the strip as a completed product, the region in the vicinity of both the edge portions of the porous sheet in the strip contracted in the completed product. Accordingly, it was found that the average aperture diameter of the porous sheet decreased on the surface of this region in the vicinity of both the edge portions and the density of the DNA probe increased in association with this decrease in average aperture diameter. With this system, it was possible to conclude that the color became considerably thick in the region in the vicinity of both the edge portions of the porous sheet in the strips of the inspection tools for nucleic acid chromatography in Examples 9 and 10.

INDUSTRIAL APPLICABILITY

The present invention is available to an inspection tool for nucleic acid chromatography usable for a diagnosis related to an infection, an allergy, and the like and for detecting a bacteria, a virus, and the like.

DESCRIPTION OF REFERENCE NUMERALS 1, 1a, and 1b: inspection tool for nucleic acid chromatography, 10: porous sheet, 13: detection surface, 14a to 14c: position marker, 15 and 15a to 15e: indication portion, 18a and 18b: end portion (of indication portion), 20: backing member, 25: attached surface, 27: back surface, 40: absorbent pad, 45: sampling portion, 50: test tube, 55: specimen, 60: target nucleic acid, 65: dye, 70: packing case, 73: inner wall, 75: inspection tool set for nucleic acid chromatography, 101, 101a, and 101b: inspection tool for nucleic acid chromatography, 110: porous sheet, 113: detection surface, 114a to 114c: position marker, 115 and 15a to 15e: indication portion, 118a to 118d: end portion (of indication portion), 120: backing member, 125: attached surface, 140: absorbent pad, 145: sampling portion, 150: test tube, 155: specimen.

The invention claimed is:

1. An inspection tool for nucleic acid chromatography, comprising:
   an elongated porous sheet that expands a sample liquid containing a target nucleic acid and detects the target nucleic acid so as to indicate the detection; and
   a backing member having an attached surface where the porous sheet is attached, wherein
   the porous sheet has a surface including a detection surface, the detection surface including a strip-shaped indication portion where a nucleic acid probe for capturing the target nucleic acid is fixed, the indication portion extending at an angle to intersect with a longitudinal direction of the porous sheet,
   the attached surface has a concave shape, and
   the porous sheet has a warped shape following the concave shape of the attached surface.

2. The inspection tool for nucleic acid chromatography according to claim 1, wherein
   the attached surface has a concave shape in a cross section that is parallel to the longitudinal direction of the porous sheet and parallel to a thickness direction of the porous sheet.

3. The inspection tool for nucleic acid chromatography according to claim 1, wherein
   the detection surface has a smaller average opening diameter of the porous sheet than an average opening diameter of the porous sheet on a surface on the attached surface side of the porous sheet in association with warping of the porous sheet.

4. The inspection tool for nucleic acid chromatography according to claim 1, wherein
   the backing member is an elongated plate, and a longitudinal direction of the backing member is parallel to the longitudinal direction of the porous sheet.

5. The inspection tool for nucleic acid chromatography according to claim 1, wherein
   the porous sheet is warped with a curvature.

6. The inspection tool for nucleic acid chromatography according to claim 5, wherein
   the porous sheet has a depression value of 1.0 to 5.0 mm.

7. The inspection tool for nucleic acid chromatography according to claim 1, wherein
   the backing member has a surface on an opposite side of the attached surface in a protruding shape complementary to the concave shape of the attached surface so as to be arched.

8. An inspection tool set for nucleic acid chromatography, comprising:
   a plurality of inspection tools for nucleic acid chromatography according to claim 1; and
   a packing case that houses the inspection tools for nucleic acid chromatography.

9. An inspection tool set for nucleic acid chromatography, comprising:
   a plurality of inspection tools for nucleic acid chromatography according to claim 7; and
   a packing case that houses the inspection tools for nucleic acid chromatography, wherein
   the respective backing members of the plurality of the inspection tools for nucleic acid chromatography are arched with different curvatures.

* * * * *

SEQUENCE LISTING

<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: Synthesized

<400> SEQUENCE: 1
tgttctctga ccaatgaatc tgc                                              23

<210> SEQ ID NO 2
<211> LENGTH: 23
<212> TYPE: DNA
<213> ORGANISM: Artificial Sequence
<220> FEATURE:
<223> OTHER INFORMATION: Synthesized

<400> SEQUENCE: 2
tggaactggg aacgctttag atg                                              23

<210> SEQ ID NO 3
<211> LENGTH: 23
<212> TYPE: DNA
<213> ORGANISM: Artificial Sequence
<220> FEATURE:
<223> OTHER INFORMATION: Synthesized

<400> SEQUENCE: 3
ttcgcttcgt tgtaatttcg gac                                              23

<210> SEQ ID NO 4
<211> LENGTH: 23
<212> TYPE: DNA
<213> ORGANISM: Artificial Sequence
<220> FEATURE:
<223> OTHER INFORMATION: Synthesized

<400> SEQUENCE: 4
aggcatccta agaaatcgct act                                              23

<210> SEQ ID NO 5
<211> LENGTH: 23
<212> TYPE: DNA
<213> ORGANISM: Artificial Sequence
<220> FEATURE:
<223> OTHER INFORMATION: Synthesized

<400> SEQUENCE: 5
tagcccagtg atttatgaca tgc                                              23

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
aggtccggta gtaatttagg tgc                                              23

<210> SEQ ID NO 7
<211> LENGTH: 23
<212> TYPE: DNA
<213> ORGANISM: Artificial Sequence

```
<220> FEATURE:
<223> OTHER INFORMATION: Synthesized

<400> SEQUENCE: 7
tattctacca acgacatcac tgc                                            23

<210> SEQ ID NO 8
<211> LENGTH: 23
<212> TYPE: DNA
<213> ORGANISM: Artificial Sequence
<220> FEATURE:
<223> OTHER INFORMATION: Synthesized

<400> SEQUENCE: 8
catctccaag aattgaccca cca                                            23

<210> SEQ ID NO 9
<211> LENGTH: 23
<212> TYPE: DNA
<213> ORGANISM: Artificial Sequence
<220> FEATURE:
<223> OTHER INFORMATION: Synthesized

<400> SEQUENCE: 9
gaaggatcgc ttttatctgg cat                                            23
```